United States Patent [19]
Giorgi et al.

[11] Patent Number: 5,470,701
[45] Date of Patent: Nov. 28, 1995

[54] METHOD FOR DETERMINING FAVORABLE PROGNOSIS IN AN HIV POSITIVE SUBJECT USING HLA-DR$^+$/CD38$^-$ CD8$^{BRIGHT}$ CELLS

[75] Inventors: Janis V. Giorgi, Woodland Hills; Lance Hultin, West Hills, both of Calif.

[73] Assignee: The Regents of the University of California, Los Angeles, Calif.

[21] Appl. No.: 22,971

[22] Filed: Feb. 24, 1993

[51] Int. Cl.$^6$ .................................................. G01N 33/569
[52] U.S. Cl. ................................................ 435/5; 435/7.24
[58] Field of Search ........................... 435/5, 7.24, 475; 422/82.08

[56] References Cited

U.S. PATENT DOCUMENTS

| | | | |
|---|---|---|---|
| 4,918,004 | 4/1990 | Schwartz | 435/7 |
| 5,108,904 | 4/1992 | Landay | 435/7.24 |
| 5,756,951 | 10/1992 | Bach et al. | 435/7.24 |

OTHER PUBLICATIONS

B. Autran et al in Janossy et al (Eds.) *Immunodeficiency in HIV Infection and AIDS*, Basel, Karger, 1992, pp. 171–184.
J. V. Giorgi et al, *Clinical Immunology and Immunopathology*, 52, 10–18, 1989.
H–N Ho et al, *Journal of Immunology*, 150, 3070–3079, 1993.
L. Kestens et al. *AIDS*, 6, 793–797, 1993.
J. B. Peter, *Use and Interpretation of Tests in Clinical Immunology*, Interstate Press, Omaha, 1990, p. 23.
H. E. Prince et al, *Diagnostic and Clinical Immunology*, 5, 188–193, 1987.
H. E. Prince et al, *Journal of Acquired Immune Deficiency Syndromes*, 4, 1227–1232, 1991.
M. J. Yagi et al, *Journal of Infectious Diseases*, 164, 183–188, 1991.

*Primary Examiner*—David Saunders
*Attorney, Agent, or Firm*—Merchant, Gould, Smith, Edell, Welter & Schmidt

[57] ABSTRACT

The subject invention involves an approach to determining the favorable prognosis of a subject infected with HIV. Specifically, the discovery involves the importance of the elevated presence of MHC class II antigen$^+$/CD38$^-$/CD8$^{bright}$ cells for the prognosis of favorable outcome in HIV-infected subjects. In one example the MHC class II antigen may be HLA-DR.

29 Claims, 16 Drawing Sheets

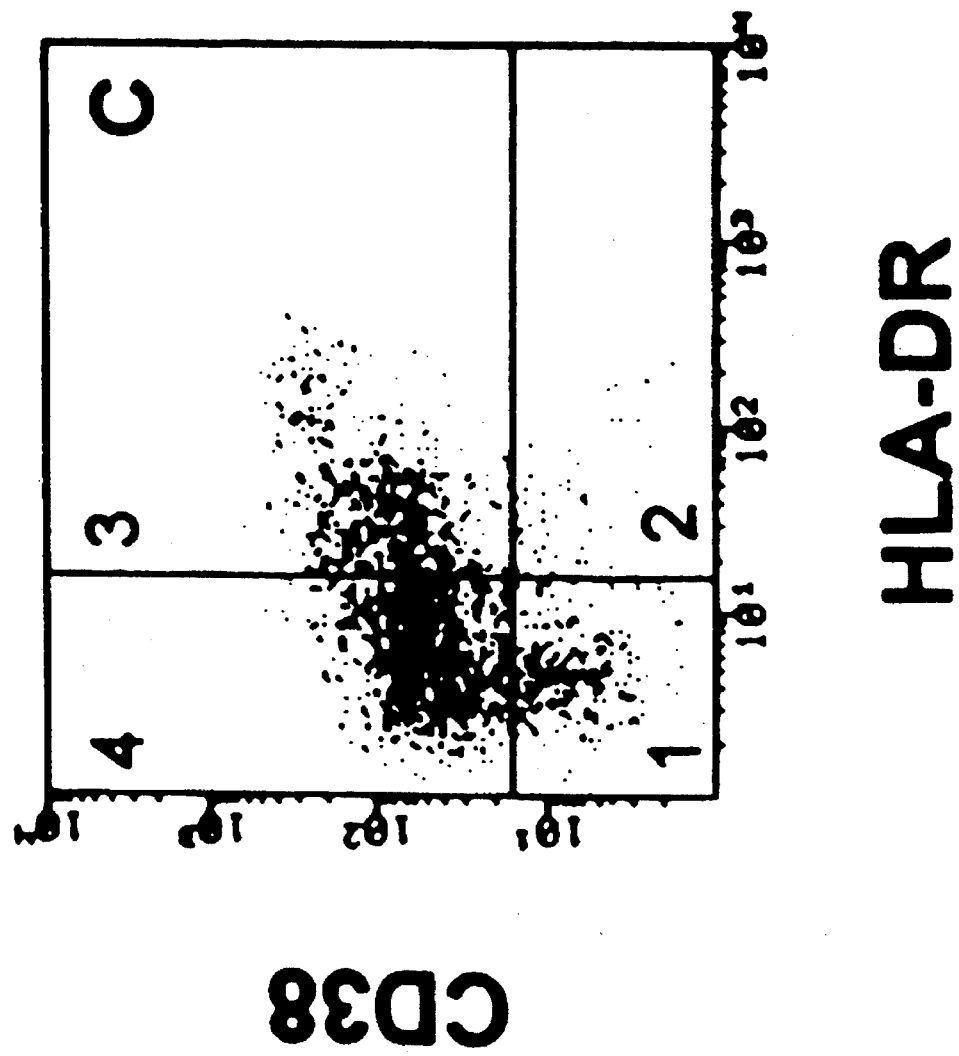

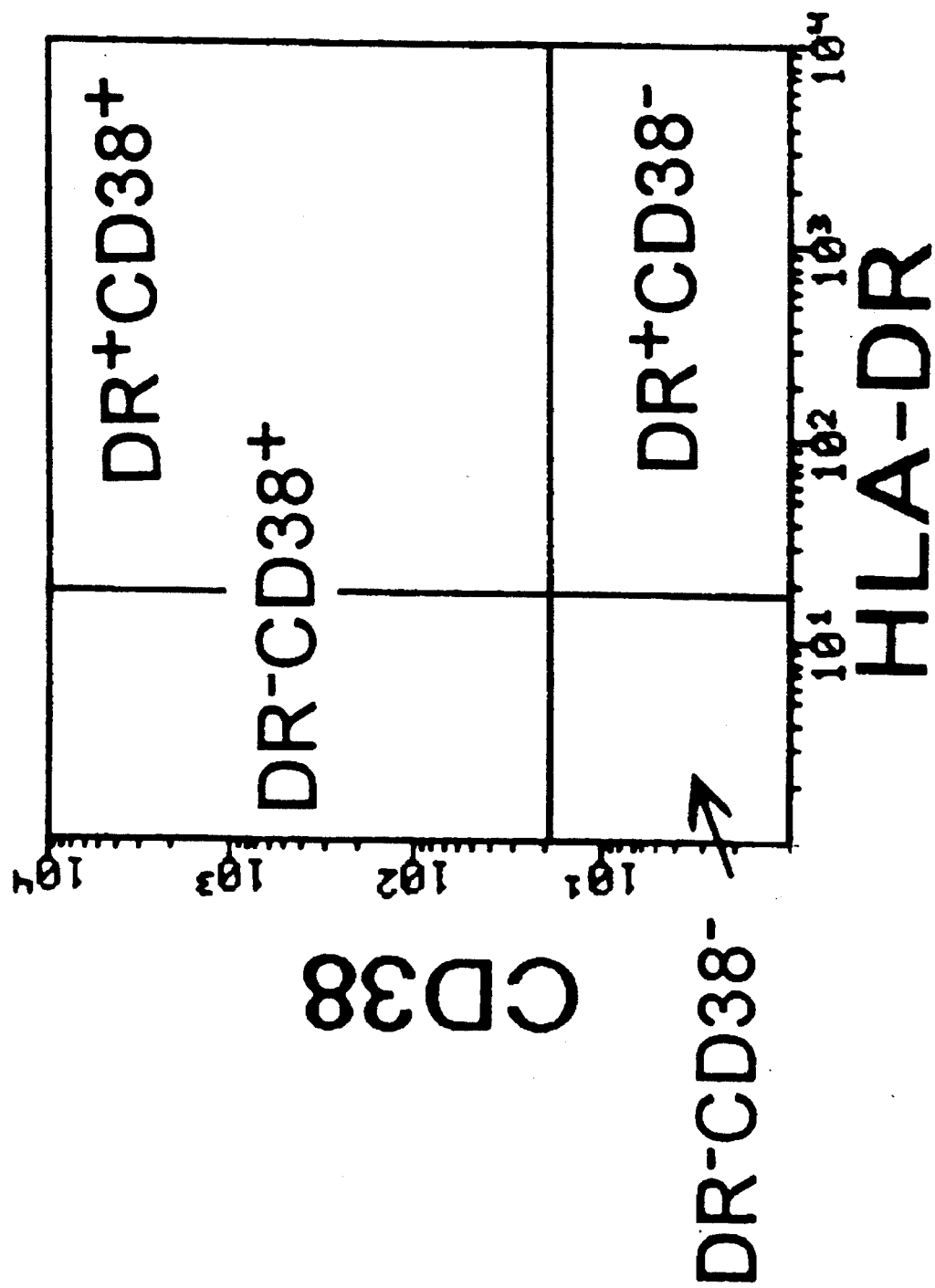

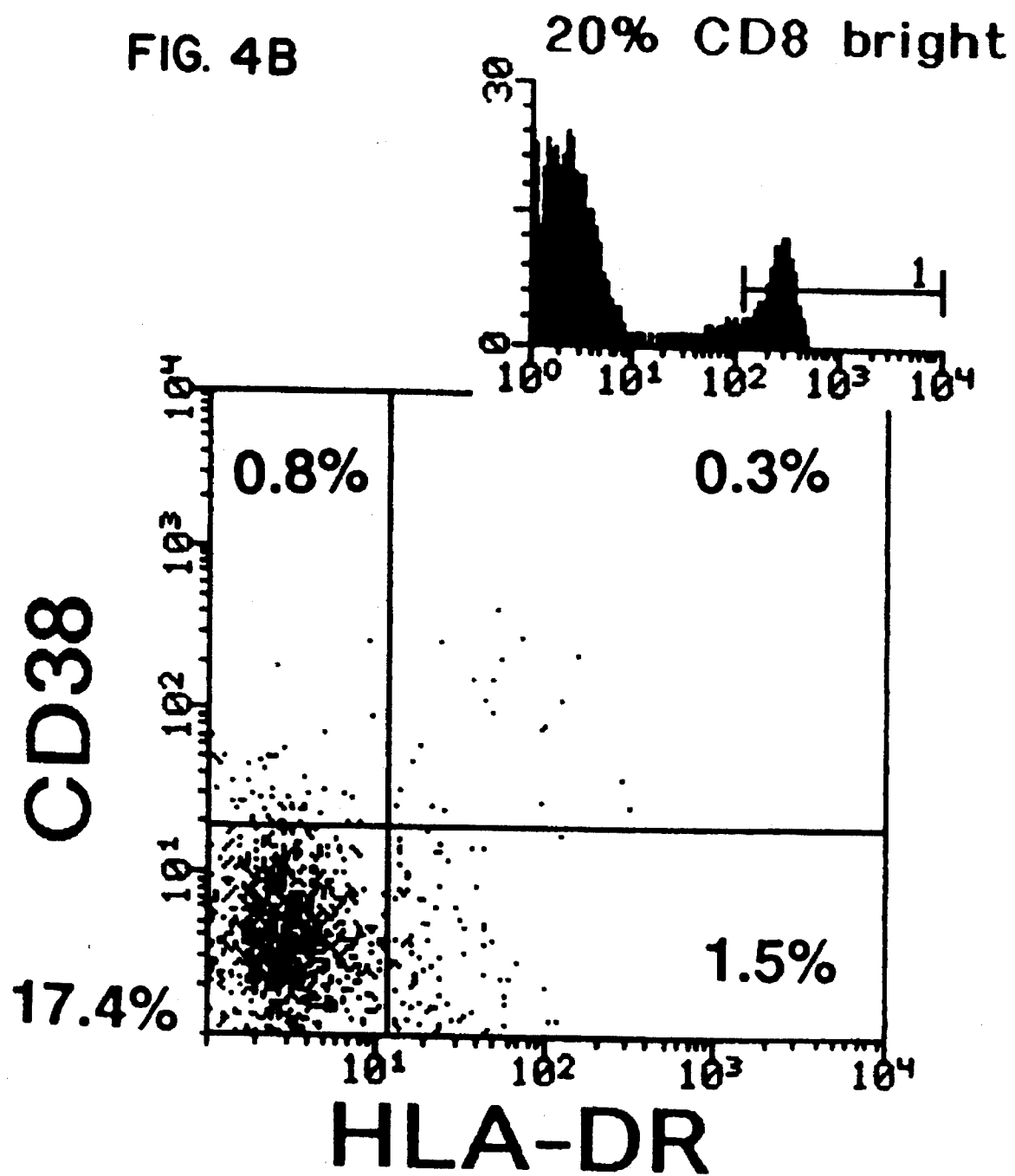

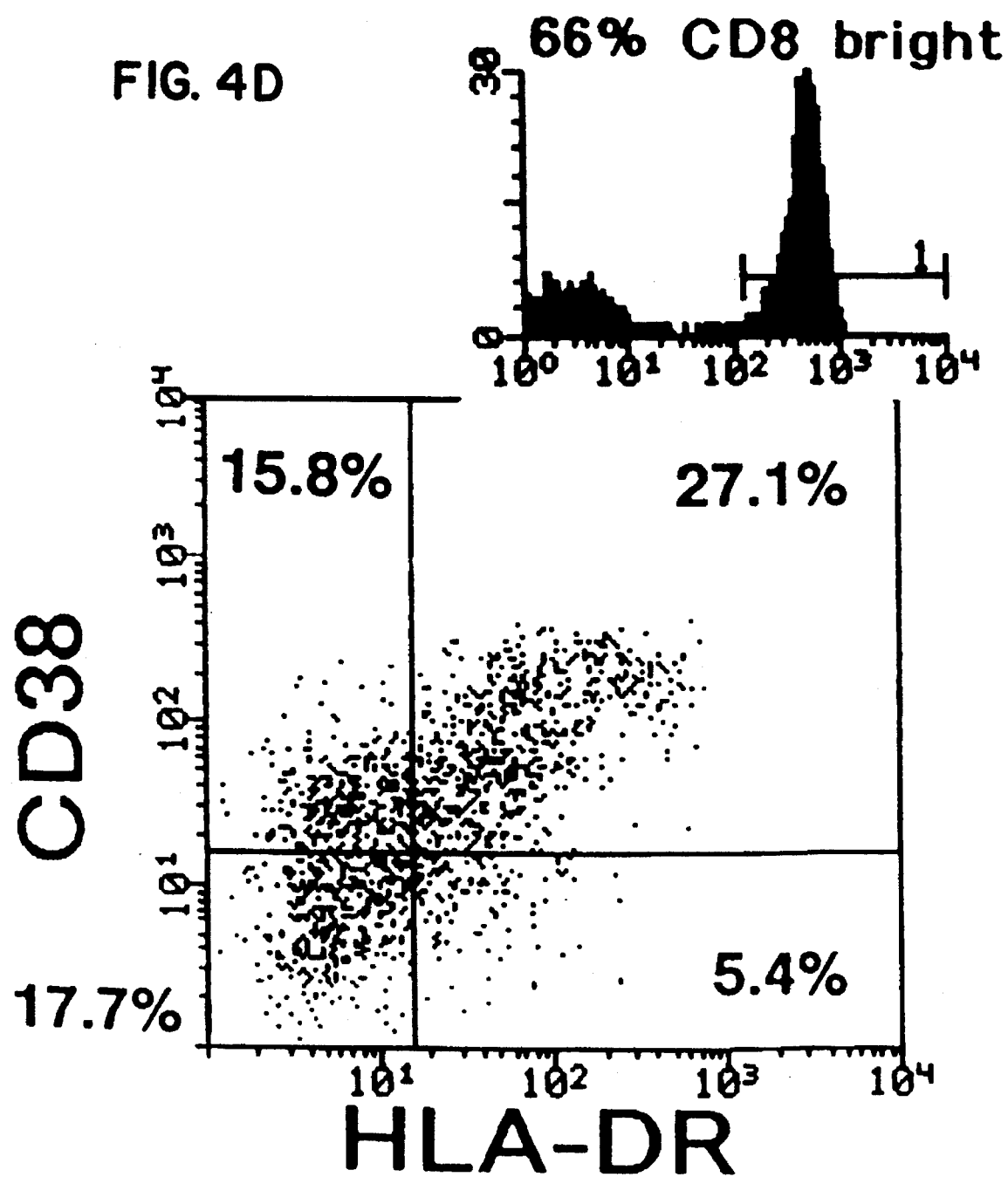

METHOD FOR DETERMINING FAVORABLE PROGNOSIS IN AN HIV POSITIVE SUBJECT USING HLA-DR$^+$/CD38$^-$ CD8$^{BRIGHT}$ CELLS

This invention was made with support under Grant Numbers AI-72631 and AI-72656 from the National Institute of Health, U.S. Department of Health and Human Resources. Accordingly, the U.S. Government may have certain rights in the invention.

Throughout this application, various publications are referenced by Arabic numerals within parentheses. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

BACKGROUND OF THE INVENTION

Presently, there are no commercially available tests to determine favorable prognosis of a patient infected with human immunodeficiency virus (HIV) the causative agent of acquired immune deficiency syndrome (AIDS).

It would be of significant value to society to be able to use information to develop relatively favorable prognosis procedures with regard to a patient infected with HIV and at risk for development of acquired immune syndrome (AIDS).

Studies have been performed to evaluate cellular markers for their ability to predict the progression of HIV disease. For example, studies have shown that CD8 positive T cells (also referred to herein as CD8$^{bright}$ cells) in HIV positive subjects express an elevated level of HLA-DR antigen on the cell surface compared with the level in healthy control subjects. Further, the number of CD8 positive T cells that also express high levels of CD38 antigen increases continually throughout HIV disease progression, and is higher in AIDS patients compared with the level in asymptomatic HIV infected subjects (4-8,56,62,63).

These studies have all evaluated cellular markers for their ability to correlate certain cellular markers with bad prognosis (65,66,73). Before the present invention, there have been no cellular markers to determine favorable prognosis.

It is important to develop cellular markers to determine favorable prognosis with regard to HIV disease and AIDS. AIDS is a disease that is projected to develop yearly in approximately 5 percent of people infected with HIV. Clinical manifestations of AIDS include opportunistic infections such as pneumocystis pneumonia, severe cytomegalovirus infection, and toxoplasmosis or certain neoplasias such as Kaposi's sarcoma and lymphoma. During all stages of HIV disease, CD4 counts are used as a laboratory marker of the extent of the immunodeficiency disease. Low CD4 counts are a strong marker of poor prognosis in HIV-infected patients (43,57–60,65,66,73).

It is believed that most people with HIV infections will ultimately develop clinical AIDS. Furthermore, death from the complications of AIDS often occurs within months or years after clinical AIDS is diagnosed.

Most HIV infected persons remain healthy for many years despite infection with HIV. Likewise, some people with past clinical diagnosis continue to live productive lives for many years after first developing clinical AIDS.

There is a need for laboratory tests that identify those HIV infected patients who are more likely to have a favorable prognosis, slower disease progression, and stable disease compared with those patients who are likely to have poor prognosis, or more rapid disease progression.

There is currently a need to develop (1) methods to identify patients who need treatment along with the appropriate type of treatment, (2) apparatus, and (3) systems to determine the characteristics of favorable prognosis associated with HIV infection.

SUMMARY OF THE INVENTION

The subject invention involves an approach to diagnosis and prognosis in HIV infected subjects. Detecting changes in the type and number of membrane antigens associated with cellular activation is important because such changes correlate with and possibly contribute to the outcome of infection with certain diseases including HIV infections.

Elevated levels of HLA-DR$^+$/CD38$^-$/CD8$^{bright}$ cells in a cell sample from a subject may be indicative of these diseases. Specifically, the discovery involves the importance of the elevated presence of MHC class II antigen$^+$/CD38$^-$/CD8$^{bright}$ cells for the prognosis of a patient infected with HIV and at risk for development of AIDS. In one example the MHC class II antigen may be HLA-DR.

The present invention provides a method for determining a relatively favorable prognosis in an HIV positive subject which comprises quantitatively detecting an elevated level of cells which substantially suppress HIV but are not substantially cytotoxic to HIV-infected cells, such elevated level being indicative of a relatively favorable prognosis.

Further, the method comprises quantitatively detecting an elevated level of cells which suppress HIV but are not cytotoxic to HIV infected cells in a biological fluid sample from a subject (49,64,74).

Alternatively, the method comprises quantitatively detecting an elevated level of HLA-DR$^+$/CD38$^-$/CD8$^{bright}$ cells in a biological fluid sample from a subject.

The present invention provides a method for determining a favorable prognosis in an HIV positive subject by measuring the level of HLA-DR$^+$/CD38/CD8bright cells in a cell sample from the subject. This method is based at least on a high cell count of CD8$^{bright}$ cells having the HLA-DR antigen but not having the CD38 antigen at levels above a threshold. (Such cells are also referred to herein as "HLA-DR$^+$/CD38$^-$/CD8$^{bright}$"). The presence of such cells would be an indicator that the patient is more likely to be able to hold their HIV disease progression in check compared with a person with a lesser number of these cells.

This invention also provides a method which comprises quantitatively determining in a sample of cells from the subject the amount of HLA-DR$^+$/CD38$^-$/CD8$^{bright}$ cells, comparing the amount of the cells so determined to the amount in a sample from an HIV negative subject or a predetermined value, the presence of a significantly different amount indicative of a favorable prognosis.

The correlation of elevated levels of HLA-DR$^+$/CD38$^-$/CD8$^{bright}$ cells to favorable prognosis is important for understanding the pathogenesis of HIV infection, in designing therapeutic agents and in designing trials directed thereto, in designing treatment plans for the patient, and providing peace of mind to the patient.

The present invention also provides a method for inhibiting HIV. This method comprises contacting HIV in the presence of HLA-DR$^+$/CD38$^-$/CD8$^{bright}$ cells under conditions such that the HIV is inhibited.

1. Denominator as Lymphocytes

The invention provides diagnosing a disease condition related to HIV infection in a human which comprises (a) obtaining a blood sample from the human, (b) determining from the sample at least one measure of a lymphocyte population having a HLA-DR$^+$/CD38$^-$ CD8$^{bright}$ cell, and (c) applying a relationship between the HLA-DR$^+$ /CD38$^-$/CD8$^{bright}$ cell population and the lymphocyte population as at least one part of a diagnostic evaluation. For example, the disease condition may be a stable disease condition.

2. Denominator as CD8$^+$ Cells

The invention further provides a method of diagnosing a stable disease condition associated with HIV in a human comprising: (a) obtaining a blood sample from the human; (b) testing the sample by determining at least one measure of a lymphocyte population, e.g., a CD8$^{bright}$ cell population having HLA-DR$^+$/CD38$^-$/CD8$^{bright}$ cells; (c) applying a relationship between the HLA-DR$^+$/CD38$^-$/CD8$^{bright}$ cell population in relation to an overall CD8$^+$ cell population as a diagnostic evaluation of a favorable prognosis of the disease condition; and (d) presenting such relationship.

3. Denominator as CD8$^{bright}$ Cells

The invention further provides a method of diagnosing a stable disease condition associated with HIV in a human comprising: (a) obtaining a blood sample from the human; (b) testing the sample by determining at least one measure of a lymphocyte population, e.g., a CD8$^{bright}$ cell population having HLA-DR$^+$/CD38$^-$/CD8$^{bright}$ cells; (c) applying a relationship between the HLA-DR$^+$/CD38$^-$/CD8$^{bright}$ cell population in relation to an overall CD8$^{bright}$ cell population as a diagnostic evaluation of a favorable prognosis of the disease condition; and (d) presenting such relationship.

4. Denominator as Activated CD8$^{bright}$ Cells

The invention further provides a method of diagnosing a stable disease condition associated with HIV in a human comprising: (a) obtaining a blood sample from the human; (b) testing the sample by determining at least one measure of a lymphocyte population, e.g., a CD8$^{bright}$ cell population having HLA-DR$^+$ /CD38$^-$/CD8$^{bright}$ cells; (c) applying a relationship between the HLA-DR$^+$/CD38$^-$/CD8$^{bright}$ cell population in relation to an overall activated CD8$^{bright}$ cell population as a diagnostic evaluation of a favorable prognosis of the disease condition; and (d) presenting such relationship.

The present invention additionally provides a method for monitoring the course of AIDS in an HIV positive subject which comprises quantitatively determining in a first cell sample from the subject the presence of HLA-DR$^+$/CD38$^-$/CD8$^{bright}$ cells and comparing the amount so determined with the amount present in a second sample from the subject, such samples being taken at different points in time, a difference in the amounts determined being indicative of change in the prognosis. A higher quantity of HLA-DR$^+$/CD38$^-$/CD8$^{bright}$ cells in the sample taken during a later time is indicative of an improved prognosis.

Additionally, the present invention provides a method of diagnosing a disease condition related to HIV in a human. This method comprises obtaining a blood sample from the human, determining from the sample at least one measure of an activated CD8$^{bright}$ cell population having HLA-DR antigen beyond a threshold, applying a relationship between the HLA-DR$^+$ cell population and certain other activated CD8$^{bright}$ cell populations as a diagnostic evaluation of the prognosis of a relatively favorable disease condition, and presenting such relationship.

The present invention includes monitoring blood samples from patients by flow cytometry to determine whether their immune system includes elevated levels of HLA-DR$^+$/CD38$^-$/CD8$^{bright}$ cells. Additionally, test kits, apparatus and systems are provided for determining favorable prognosis in a subject infected with HIV.

BRIEF DESCRIPTION OF THE FIGURES

FIGS. 1A, 1B, and 1C are representative immunofluorescence histograms of expression on CD8$^{bright}$ T cells of HLA-DR (x-axis, fluorescein isocyanate (FITC)) vs. CD38 (y-axis, phycoerythrin (PE)) Ag from (A) an HIV-seronegative control, (B) an asymptomatic HIV-seropositive subject, CD4=434/mm$^3$ and (C) an AIDS patient, CD4=48/mm$^3$.

DETAILED DESCRIPTION OF THE INVENTION

DEFINITIONS

Figure 1B:
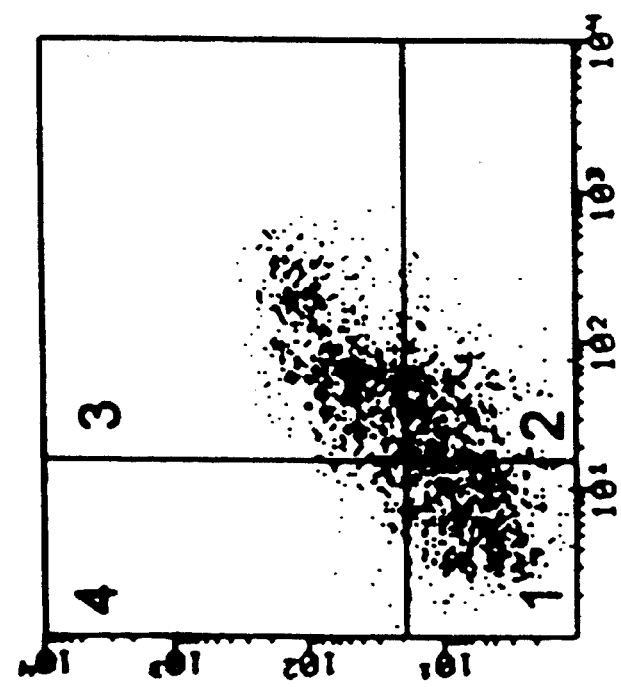

As used in this application, the following words or phrases have the meanings specified.

As used herein, "suppressing HIV" means inactivating HIV, inhibiting the replication of HIV, or merely obstructing the binding site of HIV so that it fails to bind its target.

As used herein, "favorable prognosis" is defined in two ways. One, for an asymptomatic patient, a favorable prognosis means better than average likelihood of maintenance of stable disease (i.e., stable $CD4^+$ cell levels) for longer than average AIDS-free survival. Second, for a patient diagnosed with clinical AIDS, favorable prognosis means longer than average survival between AIDS diagnosis and death.

As used herein, an "asymptomatic subject" means a subject infected with HIV but showing no symptoms generally associated with AIDS.

As used herein, "CD8 antigen" is a cell surface antigen found in large quantities on cytotoxic-suppressor T cells and in lower quantities on natural killer (NK) cells.

As used herein, "CD8 cells" mean cells that express CD8 antigen and include cytotoxic/suppressor T cells and NK cells.

As used herein, "$CD8^{bright}$ cells" mean an estimate of all T cells that express the CD8 antigen and excludes most NK cells that express the CD8 antigen.

As used herein, "HLA-DR antigen" is a cell surface antigen associated with activation.

As used herein, "CD38 antigen" is a protein molecule associated with differentiation. (9–13) It is not expressed on mature B or T cells, but is expressed on bone marrow precursors, thymocytes, plasma cells, NK cells, in vitro-activated T and B cells, and on most in vivo anti-HIV cytotoxic T cells. It has a molecular mass of about 45 to 46 kDa, does not display homology with any other known cell surface molecule, and appears to transduce activation signals.

As used herein, "threshold" means the number of cell surface molecules per cell, above which number the cells are considered to be positive and below which number the cells are considered to be negative. In relation to markers of cellular activation, a threshold is that number that best distinguishes resting cells from activated cells. In order to determine the proper thresholds for each of the cell surface molecules, one must examine the distribution of resting $CD8^{bright}$ cells in HIV negative subjects such that about 90% of the cells are judged HLA-DR antigen negative and CD38 antigen negative. Thus, HIV negative subjects will have no more than about 10% $HLA-DR^+/CD38^+/CD8^{bright}$ cells. For example, the threshold may be set at greater than 1,000 molecules/cell for each antigen and preferably between 1,000 and 6,000 molecules for HLA-DR antigen and between 3,000 and 30,000 for CD38 antigen.

As used herein, "$HLA-DR^+/CD38^-/CD8^{bright}$ cells" mean $CD8^{bright}$ cells that express HLA-DR antigen above a threshold number of molecules and express CD38 antigen below a threshold number of molecules.

As used herein, "activated $CD8^{bright}$ cells" mean $CD8^{bright}$ cells that express one or more activation markers and could include the following cell types: (1) $HLA-DR^+/CD38^-/CD8^{bright}$ cells; (2) $HLA-DR^+/CD38^+/CD8^{bright}$ cells; and (3) $HLA-DR^-/CD38^+/CD8^{bright}$ cells.

As used herein, "predetermined discriminate value" (PDV) means the ratio of the percentage or number of the $HLA-DR^+/CD38^-/CD8^{bright}$ cells relative to the percentage or number, respectively, of activated $CD8^{bright}$ cells, above which ratio the subject is considered to have a favorable prognosis and below which ratio the subject is considered to be at risk of disease progression. An example of that value is 14%. (See Example 2 below).

As used herein, the "first predetermined discriminate percentage"(IPDP) means a percentage of $HLA-DR^+/CD38^-/CD8^{bright}$ cells, above which measurement the subject is considered to have a favorable prognosis and below which measurement the subject is considered to have a poor prognosis. An example of that percentage would be 7%. (See Table III, specimen 5 of the seroconvertor slow progressors.)

The "second predetermined discriminate percentage" means a percentage (2PDP) of activated $CD8^{bright}$ cells, below which measurement the subject is considered to have a favorable prognosis and above which measurement the subject is considered to have a poor prognosis.

As used herein, the "first predetermined discriminate number" (IPDN) means the absolute number of $HLA-DR^+/CD38^-/CD8^{bright}$ cells, above which measurement is considered a favorable prognosis, and below which is a poor prognosis. An example of the number would be 223. (See Table I below.)

As used herein the "second predetermined discriminate number" (2PDN) is the absolute number of activated $CD8^{bright}$ cells below which number is considered a favorable prognosis, and above which is a poor prognosis.

As used herein, "elevated levels of $HLA-DR^+/CD38^-/CD8^{bright}$ cells" mean a quantity of $HLA-DR^+/CD38^-/CD8^{bright}$ cells above a first predetermined discriminate percentage or number.

As used herein, "precursor cells" include resting cells or any cell type that develops in vitro into an activated $CD8^{bright}$ cell.

In order that the invention herein described may be more fully understood, the following description is set forth.

THE LYMPHOCYTE POPULATIONS ACCORDING TO THE INVENTION

Cell surface molecules expressed on lymphocytes control aspects of lymphocyte function and reflect cellular differentiation state.

CD8 antigen is a protein composed of disulfide-bonded subunits of 32 and 43 kd peptides found on the surface of cytotoxic/suppressor T lymphocytes. CD8 antigen is present on 30% of peripheral blood T lymphocytes, 60% of the thymocytes and some T cell malignancies.

In the peripheral T cell compartment, the CD8 antigen largely defines the cytotoxic/suppressor subset in reciprocal fashion to CD4 antigen which defines the helper/inducer subset. Normal B cells, monocytes and granulocytes do not express surface CD8 antigen.

In addition to its expression on some T cells, CD8 antigen is expressed on a subset of NK cells. NK cells usually express a lower number of molecules of CD8 antigen per cell compared with the number of molecules of CD8 antigen on $CD8^+$ T cells. Thus, $CD8^+$ NK cells are usually $CD8^{dim}$ while $CD8^+$ T cells are usually $CD8^{bright}$.

One of the most consistent features of HIV disease is an elevation in the number of CD8 positive cells. The elevation in the number of CD8 positive cells occurs at seroconversion and persists throughout the course of HIV disease.

In HIV-infected subjects, the number of CD8 positive cells that also express HLA-DR antigen on the cell surface is elevated. In contrast, the number of CD8 positive cells that are also CD38 antigen positive increases continually throughout HIV disease progression, and is higher in AIDS patients compared with the level in asymatic HIV infected subjects.

HLA-DR membrane antigen expression in HIV disease has classically been considered to be a marker of cellular activation (52), and HIV-specific cytotoxic T lymphocytes (CTLs) have been reported to express HLA-DR antigen (53–55). HLA-DR antigen is a transmembrane class II histocompatibility antigen consisting of two glycoprotein chains of MW 34 kd and MW 29 kd. HLA-DR antigen is predominantly expressed on immunocompetent cells, primarily B cells, monocytes, macrophages, activated T cells and in low amounts on resting T cells. This class II antigen also has been demonstrated on normal dendritic cells, Langerhans cells and some epithelial cells. The induction of HLA-DR antigen expression on endothelial cells and fibroblasts by gamma interferon stimulation has also been reported. HLA-DR antigen expression is useful in the characterization of leukemias and lymphomas.

METHODS USING THE LYMPHOCYTE POPULATIONS

In one embodiment, the method comprises quantitatively detecting an elevated level of cells which substantially suppress HIV but are not substantially cytotoxic to HIV-infected cells, such elevated level being indicative of a relatively favorable prognosis.

In another embodiment, the method comprises quantitatively detecting an elevated level of cells which suppress HIV but are not cytotoxic to HIV-infected cells.

The method alternatively comprises quantitatively detecting an elevated level of $HLA-DR^+/CD38^-/CD8^{bright}$ cells in a biological fluid sample from the subject. In one embodiment, in the elevated level of $HLA-DR^+/CD38^-/CD8^{bright}$ cells, the cells have relatively greater HLA-DR antigen and relatively less CD38 antigen relative to thresholds for the HLA-DR and CD38 antigens.

This determination relative to the $CD8^{bright}$ cells as a diagnostic evaluation of the favorable prognosis of the disease.

For example, in the elevated level of $HLA-DR^+/CD38^-/CD8^{bright}$ cells, such cells have relatively greater HLA-DR antigen and relatively less $CD38^-$ antigen relative to a threshold for each of the HLA-DR and CD38 antigens, and applying this determination of elevated $HLA-DR^+/CD38^-/CD8^{bright}$ cell levels relative to the activated $CD8^{bright}$ cells as a diagnostic evaluation of the relatively favorable prognosis of the disease condition.

In another example of the method, the elevated level of $HLA-DR^+/CD38^-/CD8^{bright}$ cells is determined relative to a number of $CD8^{bright}$ cells present.

In another embodiment, the elevated level of $HLA-DR^+/CD38^-/CD8^{bright}$ cells is determined relative to a number of activated $CD8^{bright}$ cells present. In accordance with the practice of this invention, a determination of $HLA-DR^+/CD38^-/CD8^{bright}$ cells constitutes a numerator in a relationship with the number of activated $CD8^{bright}$ cells, such number of activated $CD8^{bright}$ cells constituting a denominator in the relationship.

Additionally, in one embodiment of the method a score of $HLA-DR^+/CD38^-/CD8^{bright}$ cells is determined and is represented as a first cell count, and wherein a score of activated $CD8^{bright}$ cells is determined and is represented as a second cell count such that when the number of cells in the first cell count relative to the number of cells in the second cell count is greater than a predetermined discriminate value, this is determinative of a favorable prognosis.

Further, in accordance with the practice of the method, one may relate a percentage of the $HLA-DR^+/CD38^-/CD8^{bright}$ cells relative to the percentage activated $CD8^{bright}$ cells and apply a relationship of this percentage as a diagnostic evaluation of the condition.

Additionally, a favorable prognosis of the condition may be determined in relation to an increased level of $HLA-DR^+/CD38^-/CD8^{bright}$ cells relative to the level of activated $CD8^{bright}$ cells.

In one embodiment, the method may comprise quantitatively determining in a sample of activated $CD8^{bright}$ cells from a subject the amount of $HLA-DR^+/CD38^-/CD8^{bright}$ cells, comparing the amount of the cells so determined to the amount in a sample from an HIV negative subject, the presence of a significantly higher amount being indicative of a relatively favorable prognosis.

In one example, the amount of $HLA-DR^+/CD38^-/CD8^{bright}$ cells may be determined relative to a number of activated $CD8^{bright}$ cells present. Further, the method may include determining a cell population with relatively greater HLA-DR antigen and relatively less CD38 antigen relative to thresholds for each of these antigens, and applying this determination relative to the activated $CD8^{bright}$ cells as a diagnostic evaluation of the relatively favorable prognosis of the disease condition.

In a further embodiment of the invention, the method includes determining a cell population with relatively greater HLA-DR antigen and relatively less CD38 antigen relative to a threshold, and applying this determination relative to the activated $CD8^{bright}$ cells as a diagnostic evaluation of the relatively favorable prognosis of the disease condition.

In another embodiment, the method may include a determination of $HLA-DR^+/CD38^-/CD8^{bright}$ cells which constitutes a numerator in a relationship with the number of activated $CD8^{bright}$ cells, such number of $CD8^{bright}$ cells constituting a denominator in the relationship.

The subject invention further provides a method comprising: (a) obtaining a blood sample from the human; (b) testing the sample by determining at least one measure of an activated $CD8^{bright}$ cell population having $HLA-DR^+/CD38^-/CD8^{bright}$ cells; (c) applying the measure itself or alternatively applying a relationship between the $HLA-DR^+/CD38^-/CD8^{bright}$ cell population in relation to an activated $CD8^{bright}$ cell population as a diagnostic and/or prognostic evaluation of a favorable prognosis of the disease condition; and (d) presenting such relationship.

As used herein "measure" includes a value which is expressed as an absolute number, product, quotient, ratio, percentage, a difference, or a sum.

Further, "applying a relationship" means relating at least two measures for instance as an absolute number, product, quotient, ratio, percentage, a difference, or a sum.

The method includes determining a cell population with relatively greater HLA-DR antigen and relatively less CD38 antigen relative to a threshold for each of the HLA-DR and CD38 antigens, and applying this determination relative to the activated $CD8^{bright}$ cells as a diagnostic evaluation of the relatively favorable prognosis of the disease condition.

In one embodiment of the invention, the method includes relating a percentage of the $HLA-DR^+/CD38^-/CD8^{bright}$ cells relative to the percentage of activated $CD8^{bright}$ cells, and applying a relationship of this percentage as a diagnostic evaluation of the condition.

A determination of HLA-DR$^+$/CD38$^-$/CD8$^{bright}$ cells may constitute a numerator in a relationship with the number of activated CD8$^{bright}$ cells, such number of activated CD8$^{bright}$ cells constituting a denominator in the relationship.

Further, the method provides determining a score of HLA-DR$^+$/CD38$^-$/CD8$^{bright}$ cells and representing such score as a first cell count. Further, the method provides determining a score of activated CD8$^{bright}$ cells and representing such score as a second cell count. Additionally, when the number of cells in the first cell count relative to the number of cells in the second cell count is greater than a first predetermined number, this is determinative of a favorable prognosis.

A method for monitoring the course of disease in an HIV positive subject is also provided. This method comprises quantitatively determining in a first cell sample from the subject the presence of HLA-DR$^+$/CD38$^-$/CD8$^{bright}$ cells and comparing the amount so determined with the amount present in a second sample from the subject, such samples being taken at different points in time, a difference in the amounts determined being indicative of the course of disease.

Further, a method for inhibiting HIV is also provided. This method comprises contacting HIV in the presence of HLA-DR$^+$/CD38$^-$/CD8$^{bright}$ cells under conditions such that the HIV is inhibited.

Additionally, a method for inhibiting HIV replication which comprises contacting HIV-infected lymphocytes with HLA-DR$^+$/CD38$^-$/CD8$^{bright}$ cells under conditions such that the HIV replication is inhibited is provided.

In one embodiment of the method for treating a subject suffering from symptoms associated with AIDS, such method comprises enriching the number of HLA-DR$^+$/CD38$^-$/CD8$^{bright}$ cells in the subject under conditions such that the cells inhibit the activity of HIV so as to thereby treat the subject.

For example, the step of enriching may involve upregulating the expression of HLA-DR antigens on activated CD8$^{bright}$ cells while downregulating the expression of CD38 antigens on activated CD8$^{bright}$ cells.

In another embodiment, the step of enriching the number of HLA-DR$^+$/CD38$^-$/CD8$^{bright}$ cells comprises (a) obtaining a biological fluid sample from the subject; (b) separating HLA-DR$^+$/CD38$^-$/CD8$^{bright}$ cells or precursor cells from the sample so obtained; (c) growing the cells so separated so as to multiply the number of cells so separated; and (d) replacing the cells so grown and multiplied in the same subject under conditions such that the subject exhibits an increased immunity and thereby treating the subject.

Conditions for growing cells are known in the art and vary depending upon the cell. Most practitioners are familiar with the standard resource materials which describe specific conditions and procedures. For example, cells according to the present invention may be placed in a suitable culture medium for growth and maintenance, e.g., a solution containing HIV antigens in an appropriate immunogenic formulation, and allowed to grow to confluency.

The cells may be resuspended in culture substrate, for example a sterilized buffered solution such as phosphate buffered saline (PBS) supplemented with nutrients to maintain viability. The cells may be washed with sterilized PBS using centrifugation, and then resuspended in the complete PBS at a selected density for replacement in the subject.

In place of PBS, any osmotically balanced solution, e.g. cell culture media, which is physiologically compatible with the subject may be used to suspend and replace the cells into the subject.

The subject must be appropriately prepared for replacing the cells so grown into the subject. This depends on the site within the subject used for replacing such cells. Proper blood flow and freedom from infection must be assured.

Replacement may be effected by any of the known means including, but not limited to, intravenous, intraperitoneal, intramuscular or subcutaneous administration, or the implantation of a slow-release device such as a miniosmotic pump, to the subject.

Further methods are provided for determining favorable prognosis in an HIV positive subject which comprises quantitatively detecting an elevated presence of HLA-DR$^+$/CD38$^-$/CD8$^{bright}$ cells. As shown in Table I, HIV positive asymptomatic patients exhibited elevated levels of HLA-DR$^+$/CD38$^-$/CD8$^{bright}$ cells. Additionally, in Table III, slow progressors exhibited elevated levels of HLA-DR$^+$/CD38$^-$/CD8$^{bright}$ cells approximately one year after they first tested positive for antibodies to HIV.

Additionally, a method of diagnosing a stable disease condition related to HIV in a human is provided. This method comprises obtaining a blood sample from the human, determining from the sample at least one measure of an activated CD8$^{bright}$ cell population that is HLA-DR$^+$, applying a relationship between the HLA-DR$^+$ cell population and the activated CD8$^{bright}$ or CD8 positive cell population as a diagnostic evaluation of the prognosis of a relatively favorable disease condition, and presenting such relationship.

In one embodiment, the method includes determining at least one measure of CD38 antigen in the sample, determining the HLA-DR$^+$ cell population to exclude HLA-DR$^+$ cells having the CD38 antigen, and relating such determination to the activated CD8$^{bright}$ cell population, and applying such determination as a diagnostic evaluation of the relatively favorable prognosis of the disease condition.

In another embodiment, the method includes determining at least one measure of cells with CD38 antigen, determining a cell population with relatively greater HLA-DR antigen levels and relatively lesser CD38 antigen levels relative to thresholds of HLA-DR and CD38 antigen, and applying this determination relative to the activated CD8$^{bright}$ cells as a diagnostic evaluation of the relatively favorable prognosis of the disease condition.

Further, in yet another embodiment, the method includes relating a percentage of the cells having HLA-DR antigen of relatively greater concentration relative to the percentage of activated CD8$^{bright}$ cells, and applying a relationship of this percentage as a diagnostic evaluation of the condition.

In a further embodiment, the method includes relating a percentage of the cells that have HLA-DR antigen of relatively greater concentration and CD38 antigen of relatively less concentration relative to a percentage of cells having activated CD8$^{bright}$ activated antigen and applying a relationship of this percentage as a diagnostic evaluation of the condition.

A still further embodiment includes determining at least one measure of cells with a CD38 antigen, and wherein a favorable prognosis of the condition is determined in relation to an increased level of cells presenting the HLA-DR antigen and lesser number of cells that do not express CD38 antigen above a threshold relative to the number of activated CD8$^{bright}$ cells. For example, a determination made of cells having a relatively low level of CD38 antigen and high level of HLA-DR antigen may constitute a numerator in a relationship with the number of activated $CD8^{bright}$ cells, such number of activated $CD8^{bright}$ cells constituting a denominator in the relationship.

In one embodiment, a score of cells having a presentation of a relatively high number of HLA-DR antigen molecules and a relatively low number of CD38 antigen molecules may be determined and may be represented as a first cell count, and wherein a score of activated $CD8^{bright}$ cells is determined and is represented as a second cell count such that when the number of cells in the first cell count is greater than a first predetermined number; when the number of cells in the second cell count is lower than a second predetermined number, this is determinative of a favorable prognosis.

MEASUREMENT OF THE LYMPHOCYTE POPULATIONS

Figure 7:
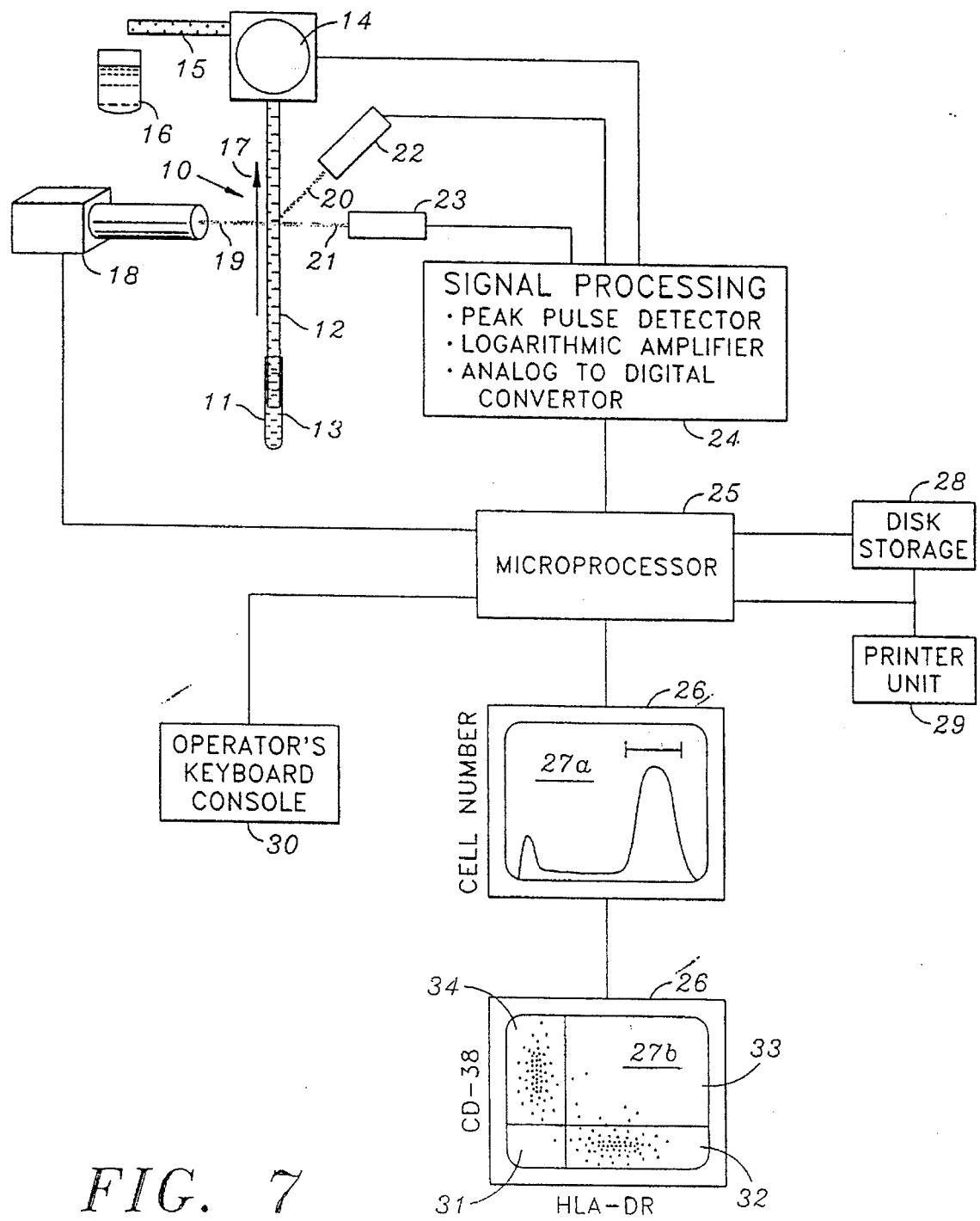
FIG. 7 is a diagrammatic illustration of the operation of a flow cytometer.

In order to effect the methods of the present invention, lymphocyte populations may be analyzed in great detail and with high efficiency using a flow cytometer generally illustrated in FIG. 7.

When cells are labeled with monoclonal antibodies conjugated with fluorescent dyes, different subpopulations can be characterized and counted. By labeling the cells with two or three different fluorescent labels, it is possible to analyze up to four or eight subpopulations simultaneously. The flow cytometer in FIG. 7 can follow sequential changes in the composition of mixed cell populations.

It would be clear that such labels may include enzymes, members of the avidin-biotin specific binding pair, and fluorochromes.

The flow cytometer is also used to measure the population of selected cells within the cell suspension directed from the reservoir 13. The cells are pumped from a reservoir 13 by a pump 14 and ejected through tube 15 into a second reservoir 16. The path of the cells are defined by arrow 17.

An illumination beam, typically a laser beam, is focused onto cells or particles passing single file in a laminar flow fluid stream. Light is scattered 20, 21 when the beam interrogates the particles. Additionally, the light can be absorbed by fluorochromes which have been bound to the cells. The fluorochromes are excited by the absorbed light (typically 488 nm) and emit light at a longer wavelength.

The scattered laser light measured at the forward low angle beam 21 correlates with cell size and the scattered light measured at 90 degrees correlates with cell granularity. The fluorescence emission is typically measured at 90 degrees.

The emitted fluorescent light and scattered light is directed by the optical system, which includes filters for wavelength selection, to the detectors, typically a photodiode for forward scatter 23 and photomultiplier tubes for fluorescence and side scatter 22. The photons of light reaching the detector produces a current pulse for each particle passing through the laser intercept.

The signal processing steps 24 that follow describe how the current pulse produced by the detectors are further processed and digitized. The current pulse is amplified and converted to a voltage pulse typically in the range of 0–10 volts. The forward scatter pulse is typically used to set a threshold voltage so that if the voltage is too low (debris), the subsequent electronics ignore the other voltage pulses from the remaining detectors.

If the forward scatter pulse is above the threshold voltage, as in the case of cells of interest, the particle is counted and subsequent electronic signals from all detectors are processed further.

The voltage pulses from each detector are then measured as a peak amplitude and/or the area under the peak pulse (integral) by a peak detector or integrator 24. The voltage pulse at the peak detector or integrator is typically held by a capacitor for measurement, then discharged and reset to await the next pulse. The peak pulse or integral pulse measurements are further processed by an amplifier.

Typically a logarithmic amplifier 24 is used for immunofluorescence measurements and a linear amplifier for measurements such as DNA content. The logarithmic amplifier produces an output signal amplitude proportional to the logarithm of the input signal amplitude so as to increase the dynamic range of the scale. Typically, 3 and 4 decade amplifiers are used to accommodate signals that vary by 1,000 to 10,000, respectively.

The amplified signal is converted to a digital signal by an analog to digital converter (ADC) 24. The ADC typically divides the amplified analog into 256 or 1024 digital values also known as channel numbers. The digitalized values are collected in memory and managed by the microprocessor 25. Information on each particle is stored in memory and includes values for each detector correlating with size, granularity and 1, 2, 3 or 4 fluorescence measurements.

The microprocessor 25 also sends signals to a video display 26 which is arranged to show histograms 27a and 27b indicative of a cell population and/or subpopulations. Sequential analysis of data to show one histogram 27b gated off another 27a can be performed. The microprocessor 25 is also associated with a disk storage system 28 for retaining data obtained from the flow of the cells 11 past the laser beam 19 and processed appropriately. Additionally, a printer unit 29 is present to provide hard copy of stored or other processed data. The microprocessor 25 is operable through a keyboard console 30 to control the flow cytometer operation, the processing of data obtained from the flow cytometer 10, disk storage 28, and representations of histogram 27 on the video display 26. Different calculations and determination may be made from the counts and characteristics of the cells 11 in their various populations and subpopulations.

Conventional measurements of lymphocyte subsets are expressed as a percentage of lymphocytes or percentage of a gated subpopulation of lymphocytes. These percentages per volume of blood (usually per $mm^3$ or per liter) are used to calculate the absolute number of the lymphocyte subset of interest per volume of blood. Absolute lymphocyte counts can be performed by standard hematological methods. Absolute lymphocyte counts can also be performed by some flow cytometers. In addition, other flow cytometers can directly measure lymphocyte subset values per volume of blood.

By using the flow cytometer principles, it is possible to separate cell subpopulations on the basis of the cell surface fluorescence or size. Such a cell separator device is a fluorescence-activated cell sorter (FACS). With such a unit, a cell suspension containing a fluorescent labeled subpopulation is passed through a very fine capillary tube such as tube 12. The end of the capillary tube 12 vibrates rapidly so that as the fluid stream emerges, it is broken into small droplets. Some of the droplets contain cells of different subpopulations. As the fluid stream passes through the capillary tube 12, it passes through a laser beam 19. Each cell 11 can be measured in terms of fluorescence or size by detectors associated with the photomultiplier tubes 22 and 23.

The operator can select cells 11 by size or fluorescence such that signals from the detectors are sent to the fluid stream so that the cells 11 become positively or negatively charged. When the stream is broken up, the charge is retained on the droplets. As the droplets pass charged plates, they are directed to either side of the stream according to the interaction between the charged droplets and the plates. Droplets which contain a first fluorescent label are deflected into a first container and droplets containing a second fluorescent label are directed into a second container. In this manner, it is possible to isolate defined lymphocyte subpopulations.

In employing the procedures, a blood sample is taken from a patient, and separated in a cell separator to obtain the leukocytes. For example, the mononuclear cells can be isolated using a density gradient.

The mononuclear cells are further separated to obtain $CD8^{bright}$ cells. Such cells or whole blood are directed through a cytometer and counts of $CD8^{bright}$ cells and populations of these cells that express or do not express the HLA-DR and/or CD38 antigens are effected. Each of these respective $CD8^{bright}$ cell populations and subpopulations characterized by HLA-DR antigen and CD38 antigen expression or absence relative to an established threshold are counted.

In accordance with the practice of the present invention an apparatus for diagnosing a disease condition related to HIV in a human by analyzing a blood sample from the human is provided. This apparatus comprises (a) means for determining from the sample at least one measure of a $CD8^{bright}$ cell population having HLA-DR antigen; (b) means for determining at least one measure of an activated $CD8^{bright}$ cell population; (c) means for applying a relationship between the HLA-DR$^+$ cell population and an activated $CD8^{bright}$ cell population as a diagnostic evaluation of a relatively favorable prognosis of the disease condition; and (d) means for presenting such relationship.

An apparatus is also provided for diagnosing a disease condition related to HIV in a human by analyzing a blood sample from the human comprising: means for determining from the sample at least one measure of an activated $CD8^{bright}$ cell population having HLA-DR$^+$/CD38$^-$/$CD8^{bright}$ cells; means for determining at least one measure of an activated $CD8^{bright}$ cell population; means for applying a relationship between the HLA-DR$^+$/CD38$^-$/$CD8^{bright}$ cell population and the activated $CD8^{bright}$ cell population as at least one of a diagnostic evaluation of a relatively favorable prognosis of the disease condition, a stable condition or an HIV suppression condition; and means for presenting the relationship.

In one embodiment, the apparatus includes a means for relating a percentage of the HLA-DR$^+$/CD38$^-$/$CD8^{bright}$ cells in a relationship to the percentage of activated $CD8^{bright}$ cells.

Further, in another embodiment, the apparatus includes a means for representing the number determination of HLA-DR$^+$/CD38$^-$/$CD8^{bright}$ cells as a numerator in a relationship with the number of activated $CD8^{bright}$ cells as a denominator in the relationship.

In a further embodiment, the apparatus includes means for representing HLA-DR$^+$/CD38$^-$/$CD8^{bright}$ cells as a first cell count; means for representing the activated $CD8^{bright}$ cells as a second cell count; means for representing at least one of a first predetermined discriminate percentage (IPDP) or first predetermined discriminate number representative of a threshold in relation to a score of the first cell count; means for representing a second predetermined discriminate percentage (2PDP) or second predetermined discriminate number (2PDN) representative of a threshold in relation to the score of the second cell count; and means for indicating when the score of cells in the first cell count is greater than the first predetermined discriminate percentage or number respectively, and when the score of cells in the second cell count is greater than a second predetermined discriminate percentage or number respectively. The apparatus can relate the scores to a predetermined discriminate value (PDV).

In one embodiment the apparatus includes means for determining at least one measure of a CD38$^-$ cell population in the sample, and means for determining the HLA-DR$^+$ cell population to exclude HLA-DR$^+$ cells that are CD38$^-$, means for relating such determination to the activated $CD8^{bright}$ cell population, and means for applying such determination as the diagnostic and/or prognostic evaluation. Further, the apparatus may include means for relating a percentage of the cells having HLA-DR antigen of relatively greater concentration and CD38 antigen of relatively less concentration in a relationship to the percentage of activated $CD8^{bright}$ cells.

In another embodiment, the apparatus may include means for representing the determination of cells having a relatively low level of CD38 antigen and high level of HLA-DR antigen as a numerator in a relationship with the number of activated $CD8^{bright}$ cells, and means for presenting such number of activated $CD8^{bright}$ cells as a denominator in the relationship.

In one embodiment the kit provides a first monoclonal antibody with a first label and which reacts with substantially all CD8$^+$ lymphocytes; a second monoclonal antibody with a second label and which reacts with a population of the selected lymphocytes; a third monoclonal antibody with a third label and which reacts with a second population of lymphocytes which are not of interest; a pan-T cell monoclonal antibody to identify CD8$^+$ cells as T cells and wherein the first population is HLA-DR$^+$, and the second population is CD38$^+$, and the lymphocyte population is $CD8^{bright}$.

Further, a kit is provided for determination of a selected cell population of lymphocytes in a sample containing a first population of the selected lymphocytes of interest and a second population which are not of interest. The kit comprises: (1) a first monoclonal antibody with a first label and which reacts with substantially all CD8$^+$ lymphocytes; (2) a second monoclonal antibody with a second label and which reacts with a population of the selected lymphocytes; (3) a third monoclonal antibody with a third label and which reacts with a second population of lymphocytes which are not of interest; and wherein the first population is HLA-DR$^+$, and the second population is CD38$^+$ and the selected lymphocyte population is $CD8^{bright}$. Further, in one embodiment the kit contains a monoclonal antibody combination that includes (1) a first monoclonal antibody, (2) a second monoclonal antibody that reacts with all T cells, e.g., CD3 monoclonal antibody. This combination will be used to determine the number of CD8$^+$ cells. This value will be used to place the threshold on the CD8 histogram to estimate the number of $CD8^{bright}$ cells. The $CD8^{bright}$ cells will be used in this method as an approximation of the CD8 T cells for the patient.

Further, in one embodiment the kit comprises: (1) a first monoclonal antibody with a first label and which reacts with substantially all the CD8$^+$ lymphocytes; (2) a second monoclonal antibody with a second label and which reacts with a population of the selected lymphocytes; and (3) a third monoclonal antibody with a third label and which reacts with a second population of lymphocytes (such as CD38+ lymphocytes) which are not of interest; and (4) beads having at least the second and third label in a predetermined quantity whereby when the beads are passed through counting means, the signal from the beads can be used to calculate the level of antigen expression on the lymphocytes.

In one embodiment, the first population is HLA-DR+, the second population as CD38+. In another embodiment, substantially all of the lymphocyte population is $CD8^{bright}$.

In a further embodiment, the kit comprises multiple bead sets, and wherein a first set has a predetermined amount of HLA-DR antigen, a second set has a predetermined amount of CD38 antigen and a third set has a predetermined amount of CD8 antigen, respectively, for use in calibrating a counting means for determining selected cell populations in a sample.

For example, the kit may include subsets of beads in each set for a series of different predetermined amounts of each of the HLA-DR, CD38, and CD8 antigens.

Different kinds of presentations of the data from the assay of the invention are possible. Such presentations may be on a video screen or hard copy or as a histogram, FACS plot, or as numerical data. The data may be suitably stored on disk.

It is necessary to calibrate a cytometer effectively to discriminate between elevated HLA-DR antigen levels and low versus high CD38 antigen levels in order to indicate relatively better prognosis. In order to achieve meaningful interpretative results, the kit includes monoclonal antibodies (mAbs) to the antigens CD8, CD38 and HLA-DR conjugated to three different fluorochromes. The fluorochrome to protein ratio (F/P ratio) of the mAb in the kit will be provided.

The F/P ratio is one of the most important parameters in immunofluorescence. If this ratio is too low, the intensity of fluorescence will be poor. The ratio should generally not be less than 1.0 because unlabelled proteins would compete with labeled proteins for binding sites, reducing the sensitivity. The upper limit is determined by a number of factors.

In the case of fluorescein, conjugation results in a marked lowering of the isoelectric point of the antibody, and conjugation may produce highly charged acidic species which tend to stick nonspecifically to cells, especially if they are fixed. Optimally, FITC-conjugated proteins have a molar F/P ratio of about 2–3 for fixed cells, and about 4–6 for intact living cells. Self-quenching due to conjugation is not a serious problem with FITC conjugates.

The molar F/P ratio for FITC may be calculated from a formula (80, 81).

Additionally, there are beads (obtained from Caribbean Bioparticles, Inc.) conjugated with at least the fluorochrome conjugated to two of the mAb. Three or more beads with estimated levels of soluble fluorescence equivalents are provided with the fluorochrome that is conjugated to HLA-DR antigen. Likewise, three or more are provided with the fluorochrome that is conjugated to CD38 antigen. The beads are run through the cytometer.

The beads are used to calculate cursor settings that are estimated to correspond to the threshold numbers of CD38 antigen and HLA-DR antigen molecules. The cursor settings are determined based on the regression lines of the beads in the kit and the effective fluorochrome to protein (F/P) ratio of the mAb in the kit. The cursors are arranged to discriminate cells that express more or less than the threshold HLA-DR antigen and/or CD38 antigen molecules. In this manner, the cytometer is set up in relation to the particular mAb being used when a sample is passed through. Cells with a fluorescence signal greater than the cursor setting that is estimated to correspond to the threshold number of molecules are scored as positive. Cells with a fluorescence signal less than the cursor setting that is estimated to correspond to the threshold number of molecules are scored negative.

A control sample using a combination of CD8 and CD3 mAbs can be used to accurately distinguish the $CD8^{bright}$ from the $CD8^{dim}$ lymphocyte populations. The CD8 mAb must use the same fluorochrome as is used in the sample used to measure the $HLA-DR^+/CD38^-/CD8^{bright}$ populations. A fluorescence distribution that is gated on the $CD3^+$ lymphocytes is analyzed for the $CD8^+$ and $CD8^-$ populations.

A cursor is positioned at the lower left edge of the $CD8^{bright}$ population. This cursor position is then used to calculate the percent of $CD8^{bright}$ cells and to gate on the $CD8^{bright}$ population in the sample used to measure $HLA-DR^+/CD38^-/CD8^{bright}$.

The percentage of $CD8^{bright}$ cells measured in this way is typically within 1%–3% of the total $CD3^+ CD8^+$ percentage.

The analytical data from the cytometer after running a sample can be expressed as a score of each of the cell counts, a relationship of each or of selected ones of the scores, or a percentage of each of or selected groups of the scores. The signals from the photomultipliers are processed by the microprocessor appropriately to present the data.

This invention is illustrated in the Experimental Details section which follows. This section is set forth to aid in an understanding of the invention but is not intended to, and should not be construed to, limit in any way the invention as set forth in the claims which follow.

EXPERIMENTAL DETAILS

EXAMPLE 1

MATERIALS AND METHODS

Subjects

Immunophenotypic data were collected on thirty-three men. Eight were HIV-seropositive asymptomatic subjects from the UCLA Multicenter AIDS Cohort Study, ten were HIV-seronegative heterosexual age matched male controls, and fifteen were men from the UCLA AIDS CARE Clinic who had been previously diagnosed with AIDS-Kaposi's Sarcoma. Only two of the AIDS patients had a previous opportunistic infection, and both had been free of any opportunistic infection for at least one year at the time of the study. Six of the men studied for immunophenotypic alterations were or had been on anti-viral medication (zidovudine).

Eleven HIV-seropositive homosexual men from the UCLA Multicenter AIDS Cohort Study (14,15) were studied for CTL activity of their FACS sorted activated $CD8^{bright}$ cells. The absolute $CD4^+$ cell numbers of these men were between 180/mm$^3$ and 663/mm$^3$.

All of these 11 individuals were asymptomatic, and none including the one individual with a $CD4^+$ cell level <200/mm$^3$ (180/mm$^3$) had clinically diagnosed AIDS. Five were known to be under anti-retroviral medication.

Blood Specimens and PBMC Preparation

For all assays, peripheral blood mononuclear cells (PBMC) were separated from fresh heparinized peripheral blood on Lymphoprep (Nycomed Pharama, Oslo, Norway) by density gradient centrifugation.

Immunophenotypic analysis

Three-color immunofluorescence analysis of HLA-DR and CD38 Ag expression on $CD8^{bright}$ cells was performed. Ficoll-hypaque separated PBMC were stained with directly labeled mAb (Becton Dickinson Immunocytometry Systems, BDIS, San Jose, Calif.): anti-HLA-DR FITC, CD38 (Leu17) phycoerythrin (PE), and CD8 (Leu2a) allophycocyanin (APC). A tube stained with a CD3 and a CD8 mAb was used to quantify the actual $CD8^+$ T cell level in each person.

Immunofluorescence analysis was performed on a dual-laser FACS 440 (BDIS). The instrument was calibrated daily using chicken erythrocytes (Riese Enterprises, Inc., Mountain View, Calif.) to standardize the fluorescence intensity measurements; data display was on a 3.5 decade log scale.

Samples were light scatter gated on lymphocytes. $CD8^+$ T cell lymphocytes, referred to here as $CD8^{bright}$ cells (16,17), were then analyzed for CD38 antigen and/or HLA-DR Ag expression. The distinction between $CD8^{bright}$ cells positive or negative for CD38 antigen and HLA-DR Ag was made on the basis of isotype matched controls.

An estimation of which $CD8^{bright}$ cells represented $CD8^+$ T cells was made for each subject by (1) analyzing the fluorescent histogram of cells stained with CD8 and CD3 mAb; (2) moving the integration cursor on the CD8-APC histogram from the far right (brightest) towards the left (dimmer) until the percentage of CD8+ cells selected was approximately equal to (within 2%) of that subject's CD8+ T cell value.

The absolute numbers of $CD8^{bright}$ cells in the HLA-DR$^-$/CD38$^-$, HLA-DR$^+$/CD38$^-$, HLA-DR$^+$/CD38$^+$, and HLA-DR$^-$/CD38$^+$ populations were calculated by multiplying the percentage of each $CD8^{bright}$ cell subset from the flow cytometer (FIG. 1) by the absolute lymphocyte count obtained from a white blood count and differential.

Figure 1A:
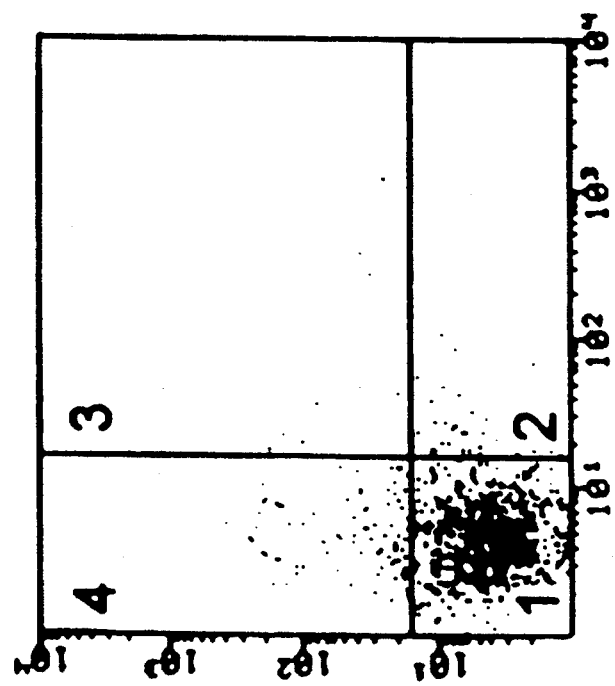

FIG. 1 are histograms showing representative immunofluorescence of expression on $CD8^{bright}$ cells of HLA-DR (x-axis, FITC) vs. CD38 (y-axis, PE) Ag from (A) an HIV-seronegative control, (B) an asymptomatic HIV-seropositive subject, CD4=434/m$^3$ and (C) an AIDS patient, CD4=48/mm$^3$. Cursors set on the isotype control tubes to include <1% of the positive events in any positive region were used to define four regions on the HLA-DR vs. CD38 histograms. The relative fluorescence intensity of HLA-DR antigen and CD38 antigen expression allowed definition of four $CD8^{bright}$ cell subpopulations: (1) HLA-DR$^-$/CD38$^-$, (2) HLA-DR$^+$/CD38$^-$, (3) HLA-DR$^+$/CD38$^+$, and (4) HLA-DR$^-$/CD38$^+$.

$CD8^+$ cell enrichment

PBMC were washed and resuspended at 60× 10$^6$ cells/ml in PBS without divalent cations. A cocktail of mAb consisting of CD4 biotin (12 g, GenTrak, Inc., Plymouth Meeting, Pa.; Cat. #0027-0704), CD16 biotin (15 g, Leu11c, BDIS), and CD19 biotin (15 g, Leu12, BDIS) was added in a total volume of 150 l. After a 10-min incubation on ice, the cells were washed once, then were incubated with avidin-FITC (BDIS) at 1 g/10$^6$ cells.

After a further 10 min incubation on ice, a 1:100 dilution of biotinylated beads (Miltenyi Biotec, GmbH, Cologne, Germany; Cat. #221-03) was added and this mixture was incubated on ice for 5 min. The cell suspension was then passed through a magnetic activated cell sorter (MACS, Miltenyi Biotec) that had been cooled to 40° C.

The unbound cells were collected. This fraction, analyzed by flow cytometry, included 1.4±0.9% (mean±SD) combined CD4$^+$, NK and B cell contamination (residual cells stained with the biotinylated mAb plus avidin-FITC); the remainder (>98%) of the lymphocytes stained with Leu2a mAb and thus were $CD8^+$ cells.

The $CD8^+$ cells were resuspended in medium (RPMI supplemented with 250 U/ml of penicillin, 250 g/ml streptomycin, 2 mM L-glutamine and 25 mM HEPES) and 10% FCS for the CTL assay.

Sorting of $CD8^{bright}$ cell subpopulations

Three-color immunofluorescence cell sorting was done on a dual-laser FACStar$^{plus}$ equipped with a 2 Watt argon ion and a 50 mW HeNe laser (BDIS) operating at 250 mW and 40 mW, respectively. Aliquots of 30×10 PBMC were stained with the following azide-free mAb: anti-HLA-DR FITC (1.9 g), CD38 PE (Leu17, 1.9 g), CD4 biotin (6 g, Gentrak), CD16 biotin (Leu11c, 15 g) and CD19 biotin (Leu12, 7.5 g) for 20 min at 4° C. in 600 l of HBSS. The cells were washed twice in HBSS.

Streptavidin APC (0.9 g, BDIS) was added and the cells were incubated for another 20 min. The cells were washed once in HBSS and resuspended in 3 ml of sorting medium (RPMI supplemented with 2 M/ml of L-glutamine, 25 mM/ml of HEPES, and 25 g/ml of gentamycin) plus 10% heat-inactivated human AB sera.

Samples were light scatter gated on lymphocytes. A single parameter histogram of APC-fluorescence was then displayed, and a gate was set selecting the negative peak of the APC-fluorescence histogram. This gated negative peak included primarily $CD8^{bright}$ cell lymphocytes, with minor contamination by erythrocytes and debris. A dual-parameter histogram of DR vs. CD38 Ag expression on the $CD8^{bright}$ cells was then displayed. Cursors were set according to the isotype-matched control tubes.

On the isotype-matched control tubes, cursors had been set that allowed <1% of cells to fall to the right of the vertical (x) cursor or above the horizontal (y) cursor. Cells to the left (x) or below (y) the cursor were designated negative (-) and those to the right (x) or above (y) the cursor were designated positive $CD8^{bright}$ cells selected based on $-/-$, $+/-$, $+/+$, and $-/+$ expression of HLA-DR and CD38 Ag, respectively, were then sorted. Extensive work revealed that CTL activity could be maintained under controlled conditions of medium, temperature, time and gentle handling.

The sheath fluid used for sorting was RPMI, cells were held and collected at 15° C. during the sort, and the sorted $CD8^{bright}$ cell subpopulations were collected in sorting medium with 20% human AB sera. All sorts were completed in 5 h. The purity of each sorted subpopulation was always greater than 95%.

Target cells

B lymphoblastoid cell lines (B-LCL) were generated from PBMC by transformation in the presence of concentrated supernatant from the EBV shedding B95-8 cell line (ATCC, Rockville, Md.) and cyclosporin A (50 g/ml; Sandoz, East Hanover, N.J.) and were maintained in RPMI 1640 medium supplemented with 10% fetal calf serum (FCS).

Four different vaccinia vectors (vSC8, vDK1, vCF21 and vAbt 140) were used to infect the autologous B-LCL. The vSC8, vDK1, and CF21 vectors were obtained from the AIDS Research and Reference Reagent Program, Division of AIDS, NIAID, NIH. The vSC8 originally from Drs. Sekhar Chakrabarti and Bernard Moss was used as a control for vaccinia killing. It is a wild type vaccinia virus strain WR that contained the lacZ gene but no HIV gene. The vDK1 originally from Dr. Daniel R. Kuritzkes carries the entire coding region of the $HIV_{IIIB}$ gag gene. The vCF21, originally from Drs. Charles Flexner and Bernard Moss, contains the reverse transcriptase domain of the $HIV_{IIIB}$ pol gene (18,19). The vAbt140, which carried the $HIV_{IIIB}$ env gene (20), was generously provided by Dr. Dennis Panicali (Therion Biologics Corp., Cambridge, Mass.). Autologous B-LCL ($2\times10^6$ cells) were infected with ten plaque forming units/cell of the appropriate vaccinia vectors and incubated in a 7% $CO_2$ 37° C. incubator for 1.5 h.

After 2 washes with RPMI media, the B-LCL were resuspended in RPMI media containing 20% FCS and incubated in 7% $CO_2$ at 37° C. for 12–16 h. After this incubation, an aliquot of $1.5\times10^6$ vaccinia vector infected cells was centrifuged into a cell pellet. The pellet was resuspended in 150 µCi (1 Ci=37 GBq) $Na_2{}^{51}CrO_4$ (NEN, Dupont, Boston, Mass.) and incubated in 7% $CO_2$ at 37° C. for 1 h. After 3 washes with cold RPMI media and 10% FCS, these target cells were resuspended in fresh media at a concentration of $5\times10^4$/ml. The viability of these cells was always >85%.

$^{51}$Cr release assay

The $^{51}$Cr release assay was set up in 96-well round-bottom plates (Falcon, Becton Dickinson Labware, Oxnard, Calif.), included maximum (Saponin) and spontaneous release (media) conditions, and utilized $5\times10^3$ target cells per well. A dose-response curve including four E:T ratios set up in triplicate was performed for each effector cell population tested. VSC8 targets were included in every assay.

E:T ratios for purified $CD8^+$ T cells were usually 50:1, 25:1, 12.5:1 and 6.25:1; those for sorted $CD8^+$ cell sub-populations were usually 20:1, 10:1, 5:1 and 2.5:1. After a 5 h incubation, the supernatants were collected and counted in a Beckman (Fullerton, Calif.) gamma counter. The spontaneous release was always <20%. The percentage of specific cytotoxicity for each condition was calculated as: {experimental release—spontaneous release/maximal release—spontaneous release}×100.

In order to compare levels of CTL activity among different experiments, especially for the sorting experiments, cytotoxicity was lytic units expressed as (LU) per $10^6$ cells (21). One LU, designated as 10% cytotoxicity because of the relatively low activity of circulating HIV-specific CTL, was determined from the dose-response curve. (Ten and 20 LU represented approximately 20% and 35% specific lysis, respectively, at an effector:target (E:T) ratio of 50:1.

HIV-specific activity was calculated as lysis of the HIV-Ag expressing targets minus lysis of vSC8-infected targets. HIV-specific CTL activity was scored positive when lysis of HIV-Ag expressing targets exceeded by 3 SD the mean of the lysis of VSC8-infected targets.

Statistical analyses

To test for difference in the absolute numbers of the four $CD8^{bright}$ T cell subpopulations between HIV-seronegative controls, asymptomatic HIV-seropositive subjects and AIDS subjects, two sample t tests were performed (22).

To evaluate whether the level of CTL activity differed among the four $CD8^{bright}$ cell subpopulations that were phenotypically defined by DR and CD38 Ag expression, an analysis of variance was used with $CD8^{bright}$ T cell subset as a fixed effect and patient as a random effect (24).

The dependent variable in this analysis was the log of the LU. Multiple comparisons were made using the Student-Newman Keuls method (25).

Most $CD8^{bright}$ cells in HIV-infected subjects express CD38 antigen and/or HLA-DR Ag Representative examples of HLA-DR (DR) and CD38 Ag expression on $CD8^{bright}$ cells of a control and two HIV-infected persons are shown in FIG. 1. Each person had a characteristic pattern of expression for these two activation-associated molecules. Four populations of $CD8^{bright}$ cells that were "positive" or "negative" for CD38 antigen and/or DR Ag expression were defined relative to the isotype control settings.

As shown in FIG. 1 and Table I, most $CD8^{bright}$ cells in HIV-seronegative control subjects expressed neither activation-associated Ag and were thus $HLA-DR^-/CD38^-$. In contrast, many $CD8^{bright}$ cells in HIV-seropositive subjects expressed either one or both activation-associated Ag. Cells with the $HLA-DR^+/CD38^-/CD8^{bright}$ phenotype were especially prevalent in asymptomatic HIV-seropositives (223±115), and less prevalent in AIDS (93±83, p=0.005).

In contrast, cells with the $HLA-DR^-/CD38^+$ phenotype were prevalent in subjects with AIDS (178±56), whereas in asymptomatic subjects (71±53), as in HIV-uninfected controls (54± 26), these cells were rare. Cells with the $HLA-DR^+/CD38^+$ phenotype were prevalent in HIV-infected subjects, regardless of disease status (144±132 in asymptomatic subjects and 253±178 in AIDS), while practically no (7±3) activated $CD8^{bright}$ cells expressing both activation Ag were present in HIV-seronegative controls.

HIV-specific CTL activity of FACS sorted populations of $CD8^{bright}$ cells phenotypically defined by HLA-DR and CD38 Ag expression:

Eleven sorts were performed. Individuals whose PBMC were sorted were those who were known to have significant lytic activity against HIV-Ag expressing targets based on a preliminary screening assay. In each sorting experiment, CTL activity of MACS separated $CD8^+$ cells and subsets of FACS sorted $CD8^{bright}$ cells, phenotypically defined by expression of DR and CD38 Ag, were tested. An example of a typical histogram of HLA-DR and CD38 Ag expression, gated on $CD8^{bright}$ T cell lymphocytes, and the purity of the sorted populations, is illustrated in FIG. 2.

Figure 2:
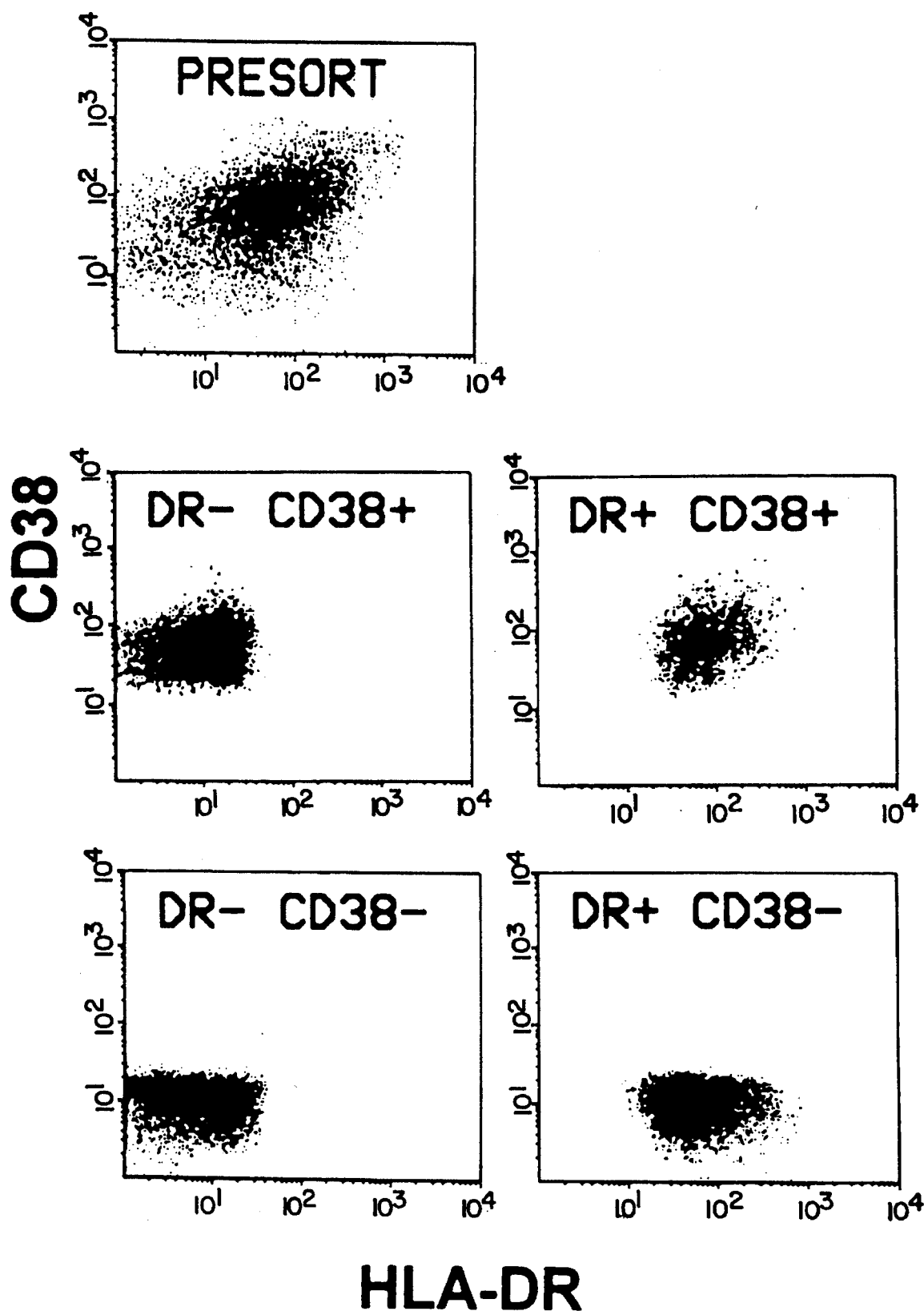
FIG. 2 is a histogram showing representative pre-sort (single large histogram, left) and post-sort (four small histograms, right) analyses.

FIG. 2 is a histogram showing the representative pre-sort (single large histogram, left) and post-sort (four small histograms, right) analysis.

Figure 3:
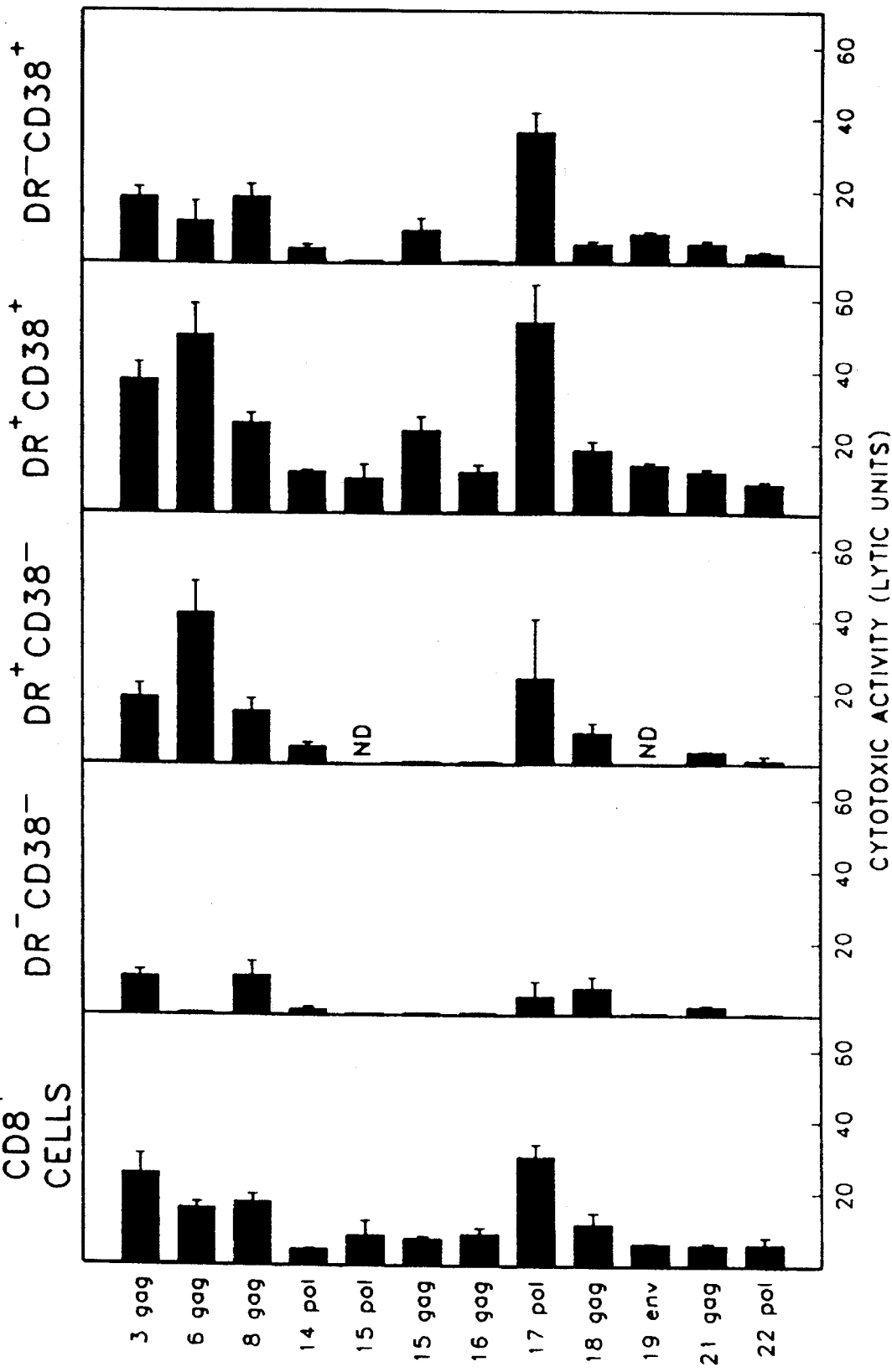
FIG. 3 is a histogram showing HIV-specific CTL activity of fluorescence activated cell sorter (FACS) sorted CD8$^{bright}$ cell subpopulations.

Complete results of the cytotoxicity assays are presented in FIG. 3. In every person tested, the activated $CD8^{bright}$ T cell population that expressed both DR and CD38 Ag had the strongest CTL activity compared with the other three sub-populations and consistently had higher activity than unsorted but purified $CD8^+$ cells. The resting $HLA-DR^-/CD38^-/CD8^{bright}$ T cell population, which predominates in HIV-seronegative controls, had very little cytotoxic activity. The $HLA-DR^+/CD38^-/CD8^{bright}$ and $HLA-DR^-/CD38^+$ $CD8^+$ cell subpopulations had intermediate levels of CTL activity with the level in these subsets generally reflecting some fraction of that present in the $HLA-DR^+/CD38^+$ sub-population.

FIG. 3 shows a histogram of HIV-specific CTL activity of FACS sorted $CD8^{bright}$ T cell subpopulations. On the y axis, subject numbers and the HIV-Ag expressed on the target is indicated. In each experiment, purified $CD8^+$ cells, prepared using the MACS, and four FACS sorted $CD8^{bright}$ T cell populations were tested. A total of eleven sorts were performed. Cells from Subject 15 were tested against both pol and gag-expressing targets in a single experiment. Cytotoxic activity (lytic units) represents lysis of the HIV-expressing targets minus lysis of the vSC8 control targets. Error bars represent 1 SD of the values obtained from triplicate wells of the $^{51}$Cr release assay. ND, not done due to low representation of the subset in the individual and recovery inadequate to test CTL activity.

As expected based on examination of the pattern of activity illustrated in FIG. 3, analysis of variance indicated that there were significant differences between CTL activity mediated by the four $CD8^{bright}$ cell subsets. The multiple comparisons analysis showed that the percentage of CTL activity in the HLA-DR$^+$/CD38$^+$ CD8$^+$/CD8$^{bright}$ cell subpopulation was significantly higher than that in other subsets, and that the CTL activity in the HLA-DR$^-$/CD38$^-$ subpopulation was significantly lower than all other subsets. Despite the clear predominance of CTL activity in the HLA-DR$^+$/CD38$^+$ subset, there was not a correlation between CTL activity and the level of HLA-DR$^+$/CD38$^+$ cells in each individual.

Thus, even though the HLA-DR$^+$/CD38$^+$ subpopulation mediated most of the activity, the level of anti-HIV-specific cytotoxic activity in an individual could not be predicted based on his level of HLA-DR$^+$/CD38$^+$ CD8$^{bright}$ cells.

In HIV infection, detectable levels of (circulating) HIV-specific CTL persist throughout the latent course of infection (2,3,26) due apparently to chronic activation of CTL as a result of the persistence of HIV (1,27). HIV-specific CTL against the structural proteins env (28,29), pol (30) and gag (29,31,32,48) have been reported.

The current work with purified $CD8^{bright}$ cells corroborates previous reports that CD8$^+$ cells in HIV-infected hosts mediate anti-HIV CTL activity against these structural proteins. It also extends previous work in that it directly examined the CTL activity of pure populations of $CD8^{bright}$ cells. Most previous work used indirect methods to demonstrate the CD8$^+$ T cell phenotype of anti-HIV directed CTL including blocking of activity by mAb (CD8 or anti-HLA class I mAb) (29,30,33), depletion of the activity by CD8 mAb plus complement treatment (34–36), and demonstration of MHC class I restricted activity (26,31,36,37).

The levels of CTL activity of the sorted $CD8^{bright}$ cell populations in this assay, compared with the levels in the MACS purified CD8$^+$ populations (FIG. 3), suggested that much of the CTL activity in the whole population was recovered in the sorted fractions.

The striking elevation of the HLA-DR$^+$/CD38$^-$/CD8$^{bright}$ subpopulation in asymptomatic HIV-seropositive subjects was notable. We originally expected that the HLA-DR$^+$/CD38$^-$/CD8$^{bright}$ subpopulation might have the greatest CTL activity because of the association of CTL with protective immunity in other viral infections. However, this did not prove to be the case. It is possible that the HLA-DR$^+$/CD38$^-$/CD8$^+$ population may have an alternate anti-HIV activity other than cytotoxicity. For example, it may be responsible for suppression of viral replication as described elsewhere (49–51).

It was somewhat surprising that the HLA-DR$^+$/CD38$^+$/CD8$^{bright}$ cell subpopulation, which had the highest CTL activity, was markedly more elevated in AIDS patients (253±178) compared with asymptomatic HIV-seropositive persons (144±132) even though our data also indicated that low CD4$^+$ cell numbers correlated with low CTL activity. The lack of correlation between the level of CTL activity and the level of HLA-DR$^+$/CD38$^+$/CD8$^{bright}$ cells indicates that flow cytometric enumeration of HLA-DR$^+$/CD38$^{+/}$ $CD8^{bright}$ cell levels cannot be used as a substitute for functional assay of anti-HIV cytotoxic activity.

We provide the first evidence that expression of CD38 Ag on $CD8^{bright}$ cells in HIV-infected people in part represents expansion of HIV-specific CTL.

EXAMPLE 2

MATERIALS AND METHODS

Subjects

Thirty-two individuals were studied who were participants in the Multicenter AIDS Cohort Study (MACS) (14, 15). Sixteen were subjects who had seroconverted and had antibodies to HIV after at least 1.5 years of participation in the MACS.

Each seroconverter had a "matched" control who was a persistently seronegative man who had samples stored at the same center on the same day that the seroconverter first had HIV antibodies detected (Specimen 3, see below). Two groups of seroconverters were selected retrospectively based on their disease progression; these are referred to in this paper as slow and rapid progressors.

Rapid progressors (n=6) were men who developed AIDS during follow-up and slow progressors (n=10) were men who remained AIDS-free during follow-up. The total follow-up times for the rapid progressors (four have died of AIDS) and slow progressors were 55±17 and 64±10 months (mean±s.d.), respectively.

Specimens

Five cryopreserved specimens that had been obtained at six month intervals from each patient were obtained from the MACS repository. Specimen 3 for each seroconverter was the seroconversion visit (i.e., the visit at which anti-HIV antibodies were first detected). Seroconversion represented approximately a 6 month window (range 3 to 8 months) between the last seronegative and first seropositive visits.

All specimens from each person and his "matched" control were thawed, stained and analyzed in a single experiment. Specimens were obtained from three of the four MACS sites, specifically Johns Hopkins University in Baltimore (n=4); Northwestern University in Chicago (n=4); and UCLA (n=8).

Flow Cytometric Study

Three-color immunofluorescence analysis was performed on a FACStar$^{Plus}$ (Becton Dickinson Immunocytometry System, Inc., BDIS, San Jose, Calif.) equipped with a 2 Watt argon ion laser and a 50 mW helium neon laser operating at 250 mW and 40 mW, respectively.

Cryopreserved samples were stained using monoclonal antibodies (mAbs) against CD38 antigen [phycoerythrin (PE)-Leu 17], HLA-DR [fluorescein isothiocyanate (FITC)-HLA-DR] and CD8 [allophycocyanine (APC)-Leu-2]; mAbs were purchased from BDIS.

Measurement of p24 Antigen

Free and total serum HIV p24 antigen (p24), including dissociated p24 from immune complexes by acid pre-treatment (67) were measured in a solid-phase enzyme-linked immunosorbent assay (duPont, Wilmington, Del.).

Statistical Analyses

Repeated measures analysis of variance (ANOVA; SAS) was used to analyze changes in the subsets in the slow and rapid progressors over time. The subset values were log transformed in order to meet assumptions of the analysis. In our initial analysis we considered the two seroconverter groups separately.

The results of this analysis indicated whether the subset levels changed over time. All p-values are two-sided. In a second group of analyses, each progression group that showed significant change in a subset over time in the initial analyses was analyzed separately in order to compare the subset levels at visits 3, 4 and 5 with the average of the levels for the subset at visits 1 and 2.

Our third analysis included all seroconverters and included progression status as a grouping variable and visits as the repeated variable; the results from this analysis indicated whether the pattern of change differed in the two groups.

Wilcoxon rank sum tests (23) were used to test for differences in the percentages of two subsets of differentiated CD8 cells at visit 5 in slow and rapid progressors.

Serum p24 and Disease Progression in Seroconverters

Table II illustrates the serum p24 status at each visit and the clinical outcome of the six rapid progressors. Serum p24 was detectable in five out of six patients in the rapid progressor group and in none of the slow progressors. The mean duration from seroconversion to diagnosis of AIDS for the rapid progressors was 42 months (range from 19 to 61 months).

Four out of six rapid progressors have died. None of the slow progressors developed AIDS or died during follow-up (64±10 months).

CD4 Decrease and CD8 Increase in Rapid and Slow Progressors

Table III summarizes the alterations of CD4 and CD8 cell levels in this longitudinal study. There was a decline in CD4 cell number in both the rapid and slow progressors at the time of and after seroconversion. The decline was greater in the rapid progressors than in the slow progressors. In contrast, there was an increase in total activated $CD8^{bright}$ T cells at the time of and after seroconversion, and the increase was similar in the rapid and slow progressors.

Figure 4C:
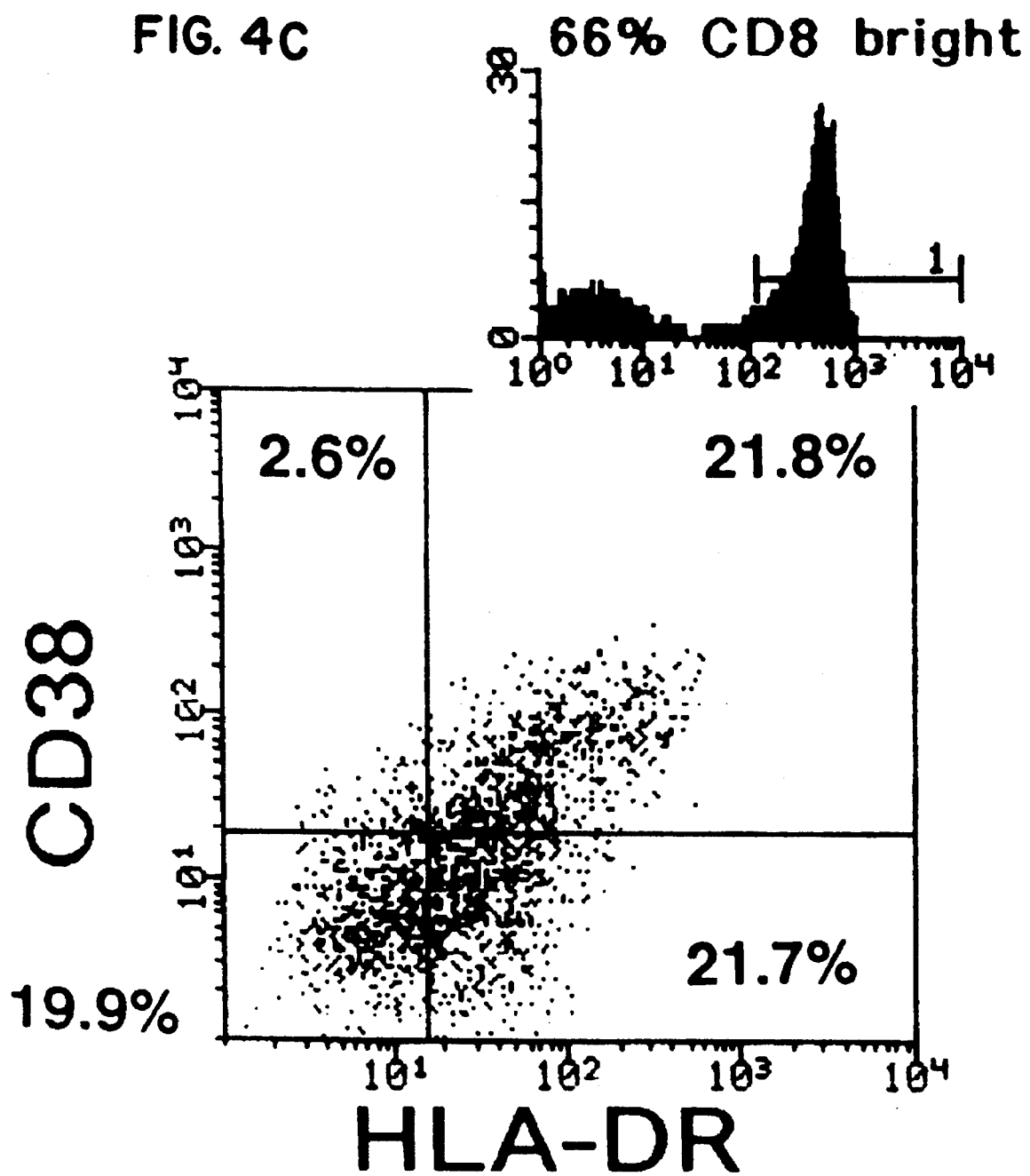
FIG. 4. Flow cytometry analysis: (A) template for the definition of the four CD8$^{bright}$ T cell subpopulations; (B) representative HIV-seronegative control; (C) representative slow progressor; (D) representative rapid progressor. (B-D) CD8$^{bright}$ T cells were selected (see insets) and the fluorescence staining with FITC-anti-HLA-DR and PE-CD38 monoclonal antibody were displayed. The numbers on histograms B-D represent the percent of lymphocytes with each of the four phenotypes, i.e., HLA-DR$^-$/CD38$^+$ CD8$^{bright}$ (DR$^-$ CD38$^+$), HLA-DR$^+$/CD38$^+$ CD8$^{bright}$ (DR+CD38+), HLA-DR$^-$ /CD38$^-$ CD8$^{bright}$ (Dr$^-$ CD38$^-$), and HLA-DR$^+$/CD38$^-$ CD8$^{bright}$ (DR$^+$CD38$^-$).

Alterations in the $CD8^{bright}$ Cells Defined by Expression of HLA-DR antigen and CD38 antigen in Rapid and Slow Progressors Three-color immunofluorescence measurements were used to quantify expression of HLA-DR and CD38 antigens on $CD8^{bright}$ cells of all the subjects at all 5 visits. A representative sample of histograms from a seronegative subject, a slow progressor seroconverter, and a rapid progressor seroconverter are shown in FIG. 4. These histograms were obtained from the Visit 5 specimens (Table III). Both rapid and slow progressor seroconverters showed marked activation of $CD8^{bright}$ cells. (FIG. 4C and 4D and Table III, last 3 columns.) Table III summarizes the alterations in the four subsets of CD8 cells defined by expression of HLA-DR and CD38 antigens during the two years around seroconversion. There was an elevation in the number of activated $CD8^{bright}$ cells represented by cells that expressed HLA-DR antigen and/or CD38 antigen.

Figures 5A, 5B:
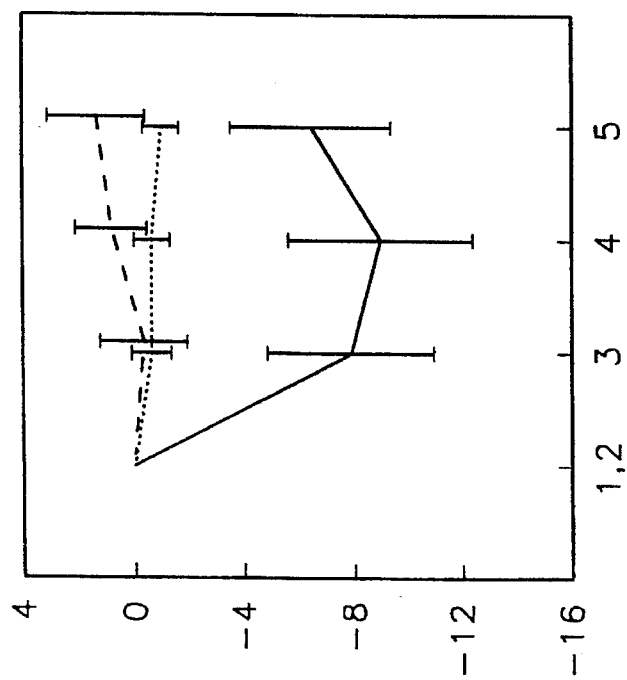
FIG. 5. Percentage difference from the baseline of the four CD8$^{bright}$ cell subsets defined by expression of HLA-DR or CD38. Percentage difference was calculated as the difference between the baseline value of the subset (mean of specimens 1 and 2) minus the subset value of specimen 3 (seroconversion visit), 4 or 5. Values shown are mean ± SEM of the groups: seronegative (...), slow progressors (———), rapid progressors (____). (A) HLA-DR$^-$/CD38$^-$ CD8$^{bright}$, (B) HLA-DR$^+$/CD38$^{-1\ /CD}$8$^{bright}$, (C) HLA-DR$^-$/CD38$^+$/CD8$^{bright}$, and (D) HLA-DR$^{-\ /CD}$38$^+$/CD8$^{bright.}$ FIG. 6. The percentage of two subpopulations of activated CD8$^{bright}$ cells expressed as the percentage of all activated CD8$^{bright}$ cells (defined as the sum of cells that expressed either HLA-DR and/or CD38): (A) HLA-DR$^+$/CD38$^-$/CD8$^{bright}$ and (B) HLA-DR$^-$/CD38$^+$/CD 8$^{bright}$ cells. Each point represents the percentage for one subject approximately 12 months after the first seropositive test.
Figure 5D:
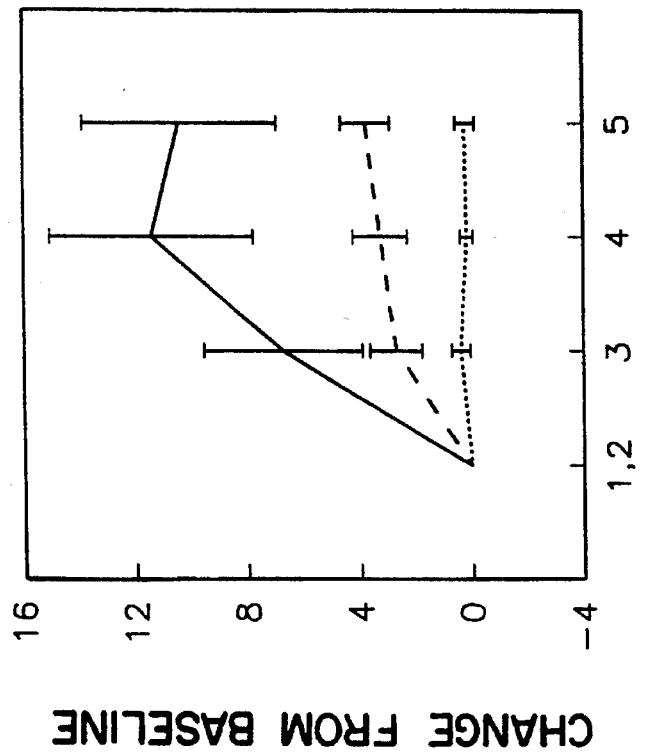
Figure 5C:
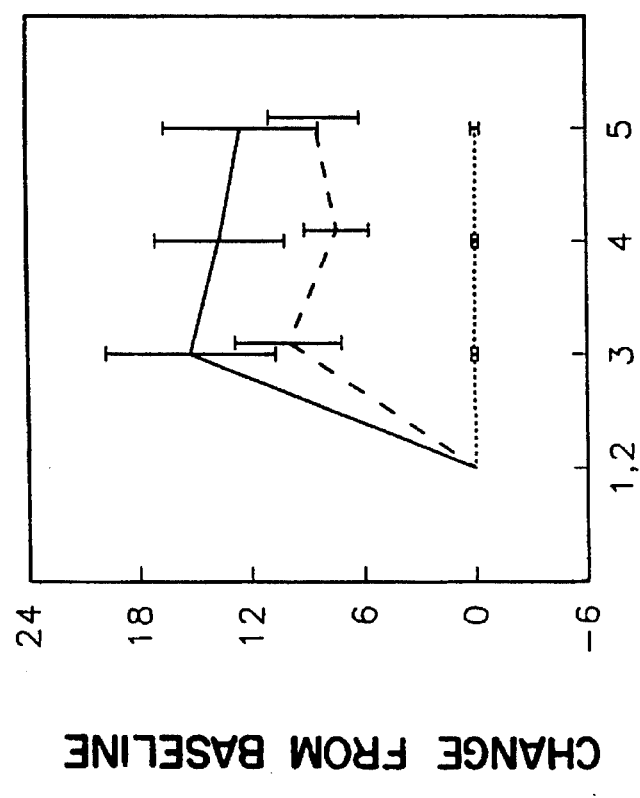

The significance of these changes in $CD8^{bright}$ cell subsets over time was determined by repeated measures analysis of variance (ANOVA), as described in the Materials and Methods, and FIG. 5 illustrates the change in each of the four $CD8^{bright}$ subsets over time depicted as the change at visit 3, 4 and 5 from the baseline level.

The results from the repeated measures ANOVA for HLA-DR$^-$/CD38$^-$ (i.e., resting) CD8 cells e.g., $CD8^{bright}$ cells indicated a significant change over time for the rapid progressors ($p=0.05$), and this decrease in the level of resting $CD8^{bright}$ cells over time is apparent in FIG. 5. There was no change in the level of this subset for the slow progressors. In a separate analysis of the rapid progressor group, this group had significant decreases in the level of resting $CD8^{bright}$ cells at visits 3, 4, and 5 over baseline ($p=0.04$, 0.05, 0.04, respectively).

The results from the repeated measures ANOVA from the HLA-DR$^+$/CD38$^-$/CD8$^{bright}$ subset indicated that there was a change over time for the slow progressors ($p=0.0001$) but no change for the rapid progressors ($p=0.22$). When the slow progressors were analyzed separately, we found that the slow progressors had significant increases in this subset at visits 3, 4, and 5 ($p=0.002$, 0.0002, 0.0005, respectively).

For HLA-DR$^+$/CD38$^+$/CD8$^{bright}$ cells, the analysis found significant changes over time for both the slow and rapid progressor ($p=0.0001$), but there was no evidence that the pattern of change differed in the two groups. In separate analyses, both groups had significant increases at visits 3, 4, and 5 when compared to the baseline (all p value<=0.005). Likewise, for HLA-DR$^-$/CD38$^+$/CD8$^{bright}$ cells, the results showed significant changes over time for both the slow ($p=0.0001$) and the rapid progressor ($p=0.0002$) groups.

In the separate analyses, both groups had significant increases in this subset at visits 3, 4, and 5 when compared to the baseline (all p values<=0.02, for rapid progressors and all p values<=0.001 for slow progressors).

Figure 6A:
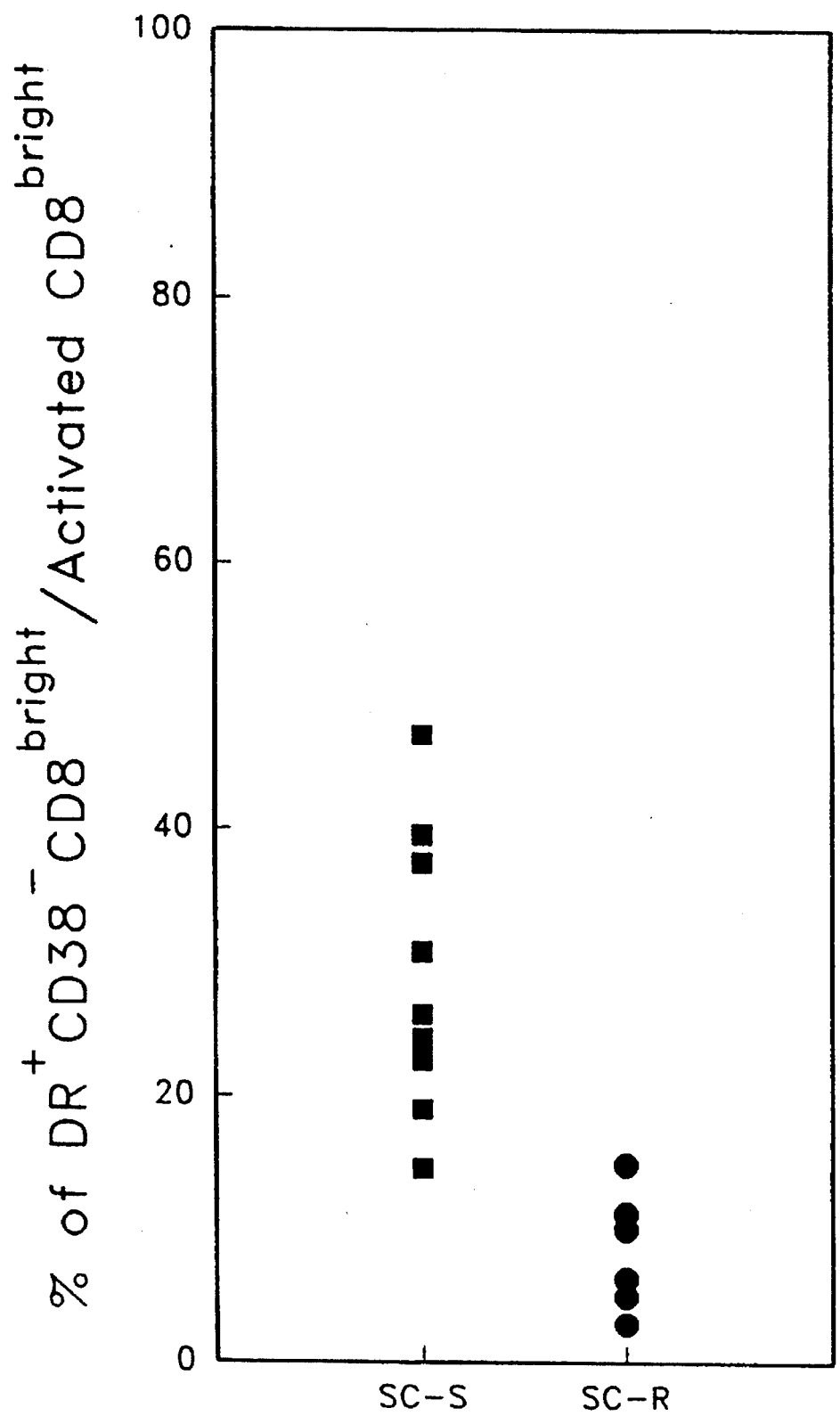

The Proportion of Activated Lymphocytes with the HLA-DR$^+$/CD38$^-$/CD8$^{bright}$ Phenotype was Associated with Slower Progression to AIDS In an effort to attempt to utilize the elevation in the HLA-DR$^+$/CD38$^-$/CD8$^{bright}$ cells as a marker of prognosis, we attempted several ways of expressing the data including (1) absolute number (abs. no.), percentage (Table III), (2) proportion of the subset within the $CD8^{bright}$ cells (abs. no. HLA-DR$^+$/CD38$^-$/CD8$^{bright}$ divided by abs. no. $CD8^{bright}$) and (3) proportion of the subset within the activated $CD8^{bright}$ cells (HLA-DR$^+$/CD38$^-$/CD8$^{bright}$ divided by activated $CD8^{bright}$ cells; FIG. 6).

The final way of expressing the data, i.e., the proportion of the HLA-DR$^+$/CD38$^-$/CD8$^{bright}$ divided by activated $CD8^{bright}$ cells (FIG. 6A), provided a clear and distinguishable difference between slow and rapid progressors. Thus, in the slow progressors, this proportion was substantial (range 14.5%–47.1%) one year postseroconversion, whereas this proportion represented only a small fraction (range 3%–14.8%) of the activated $CD8^{bright}$ cells in the rapid progressors.

In FIG. 4B, the percentage of HLA-DR$^+$/CD38$^-$/CD8$^{bright}$ cells from a patient with 20% $CD8^{bright}$ cells (this patient was HIV-seronegative) was in the range of about 1.5%. In FIG. 4C, the percentage of HLA-DR$^+$/CD38$^-$/CD8$^{bright}$ cells from a patient with 66% $CD8^{bright}$ cells (this patient was asymptomatic for HIV related conditions) was in the range of about 21.7%. In FIG. 4D, the percentage of HLA-DR$^+$/CD38$^-$/CD8$^{bright}$ cells from a patient with 66% $CD8^{bright}$ cells (this patient was symptomatic for HIV related conditions) was in the range of about 5.4%. Since the HLA-DR$^+$/CD38$^-$/CD8$^{bright}$ cell level was elevated in FIG. 4C, this patient fared much better than that whose cell level is depicted in FIG. 4D. Those whose activated $CD8^{bright}$ cells level predominantly fall within the bottom right quadrant of the graph have a relatively better prognosis than those whose activated $CD8^{bright}$ cells fall predominantly in the two upper quadrants.

Moreover, as stated above the numerical value of the HLA-DR+/CD38$^-$/CD8$^{bright}$ cell level of the bottom right quadrant represents the score of cell counts, i.e. a score of cells having a presentation of a relatively high number of HLA-DR antigen and relatively a low number of CD38 antigen may be determined and may be represented as a first cell count, as described in the DETAILED DESCRIPTION herein above.

As expected, because the values between the two groups were essentially non-overlapping, the difference between the values in the groups was significant (p=0.002). The individual in the rapid progressor group who had 14.8% HLA-DR$^-$/CD38$^-$/CD8$^{bright}$ phenotype at visit 5 was the last one to develop AIDS (61 months after seroconversion), never had detectable p24 (either free or complexed), and is still alive with a CD4 number of 330 after 6 years of follow-up.

Figure 6B:
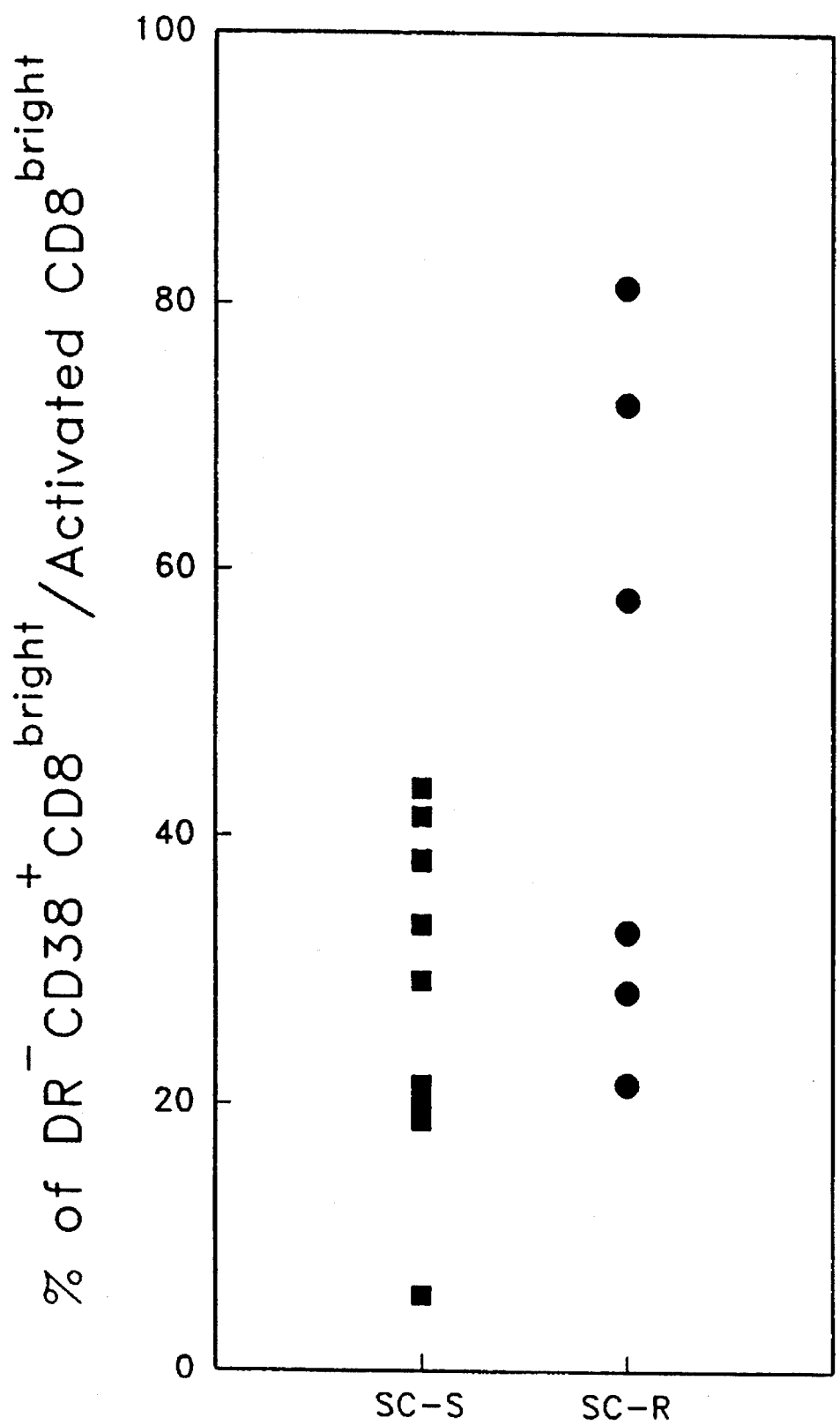

For comparison, FIG. 6B illustrates that the HLA-DR$^-$/CD38$^+$/CD8$^{bright}$ subset was dramatically elevated in some of the rapid progressors, but this change (the ratio of the number of this subset relative to the total activated CD8$^{bright}$ number) did not reach statistical significance when the groups were compared. In this study, absence of preferential elevation in the HLA-DR$^+$/CD38$^-$/CD8$^{bright}$ subpopulation was associated with rapid progression to AIDS.

Cellular immunity plays an important role in the outcome of acute virus infection (68). Adoptive transfer experiments indicate that CTL provide protection for some viruses (69, 72). MHC class I restricted HIV specific CD8 CTL are present in the circulation of HIV-infected people (49), but the contribution of these anti-HIV directed cells to the outcome of HIV disease is controversial (38–44,46,47).

The data herein show that total CD8$^+$ cell numbers increase at the time of HIV-seroconversion and thereafter, and this is in agreement with our previous studies and those of others (58,61,7). The expression of HLA-DR antigen on many of these CD8$^+$ cells suggested that they were activated (75,52,45). Activation of CD8$^+$ cells was also demonstrated by the expression of the CD38 antigen, a molecule involved in a newly defined activation pathway (10,13), although, in part, expression of CD38 antigen could also reflect lymphocyte immaturity (5).

The proportion of activated CD8$^{bright}$ cells with the HLA-DR$^+$/CD38$^-$ phenotype significantly increased in slow progressors at and after seroconversion, but not in the rapid progressors. In contrast, the degree of elevation of HLA-DR$^-$/CD38$^+$/CD8$^{bright}$ subset and of the HLA-DR$^+$/CD38$^+$/CD8$^{bright}$ subset was slightly but not significantly higher in the rapid compared with the slow progressors.

These results indicate that the pattern of CD8$^{bright}$ cell subset change at and after seroconversion may predict disease outcome. In particular, the fraction of the activated CD8$^{bright}$ T cells with the HLA-DR$^+$/CD38$^-$ phenotype may serve as an indicator of favorable prognosis with respect to the outcome in HIV infection.

The data herein shows that a phenotypically defined subset of CD8$^{bright}$ cells may be responsible for effective anti-HIV immunity.

Therefore, this change could serve as a diagnostic marker to predict good outcome in HIV-seropositive individuals.

Five of the 16 seroconverters (31%) that we studied had detectable p24, which is similar to results reported in the literature (76,79). All of these five were rapid progressors. Our data shows that only one seroconverter (rapid progressor 3, Table II) had detectable free p24 prior to seroconversion.

Free p24 appears early and transiently (for 1–2 weeks) at acute HIV infection (76,79), and was not detected pre-seroconversion in most of the subjects we studied. Reappearance or persistence of p24 seems to correlate with clinical and immunological deterioration (77), and this trend was apparent in the subjects we studied. Rapid progressor 6 and all of the slow progressors (n=10) did not have detectable p24 up to one year post-seroconversion, and low viral activity probably contributed to their relatively slower disease progression.

The slow progressors did not have detectable virus production in the serum p24 assay. Thus, HLA-DR$^+$/CD38$^-$/CD8$^{bright}$ cells may have protected against disease progression in the slow progressors by controlling virus replication. The data shows that the expanded number of circulating HLA-DR$^+$/CD38$^-$/CD8$^{bright}$ cells that appear after seroconversion may have contributed to protection against disease progression in the slow progressors.

In the rapid progressors, the failure to develop HLA-DR$^+$/CD38$^-$/CD8$^{bright}$ cells may have contributed to the failure to control HIV replication and thus to subsequent decline in CD4 cells.

EXAMPLE 3

Assume the threshold of the number of molecules of HLA-DR antigen required to score CD8$^{bright}$ cells as HLA-DR$^+$ is 2,400.

Assume the threshold number of molecules of CD38 antigen required to score CD8$^{bright}$ cell as CD38$^+$ is 15,000.

Assume the effective F/P ratio of HLA-DR mAb conjugated with fluorochrome 2 is 1.5 and the effective F/P ratio of CD38 mAb conjugated with fluorochrome 3 is 2.0 as calculated using methods known in the art.

METHOD

Run three or more beads conjugated with estimated quantities of fluorochrome 2 and three or more beads conjugated with fluorochrome 3. Develop regression lines of channel number (x) versus equivalent soluble fluorescent molecules (ESFM) (y) as shown in the plots (■, ●). Identify sensitivity of instrument (o) to allow verification that selected thresholds are above these points.

Calculate ESFM corresponding to threshold number of molecules based on effective F/P ratios.

In the example shown:

| | |
|---|---|
| Fluorochrome 2: | 2,400 molecules of HLA-DR × 1.5 F/P = 3,600 ESFM of fluorochrome 2 |
| Fluorochrome 3: | 15,000 molecules × 2.0 F/P = 30,000 ESFM of fluorochrome 3 |

Determine channel numbers corresponding to threshold ESFM for mAb 2 and mAb 3 and set instruments x and y cursors to quantitate the number of CD8$^{bright}$ cells positive and negative for expression of HLA-DR and/or CD38 antigen.

Run at least one healthy control to verify functionality of settings. Number of cells positive for both activation antigens should be less than 10% of all CD8$^{bright}$ cells.

Run HIV positive specimens as described in Example 2.

ADVANTAGES OF THE INVENTION

The subject invention involves an approach to an AIDS prognosticator different from those described previously. We have determined changes in the type and number of membrane antigens associated with cellular activation because identification of such changes correlate with and possibly contributes to the outcome of infection with HIV. Specifically, the discovery involves the importance of the elevated presence of HLA-DR$^+$/CD38$^-$/CD8$^+$ cells for good prognosis for AIDS.

The correlation of elevated levels of HLA-DR$^+$/CD38$^-$/CD8$^+$ cells to good prognosis is important for understanding the pathogenesis of HIV infection and in designing therapeutic agents and trials directed thereto and in designing treatment plans for patients.

Calculations for Prognosis Determination

Figure 8:
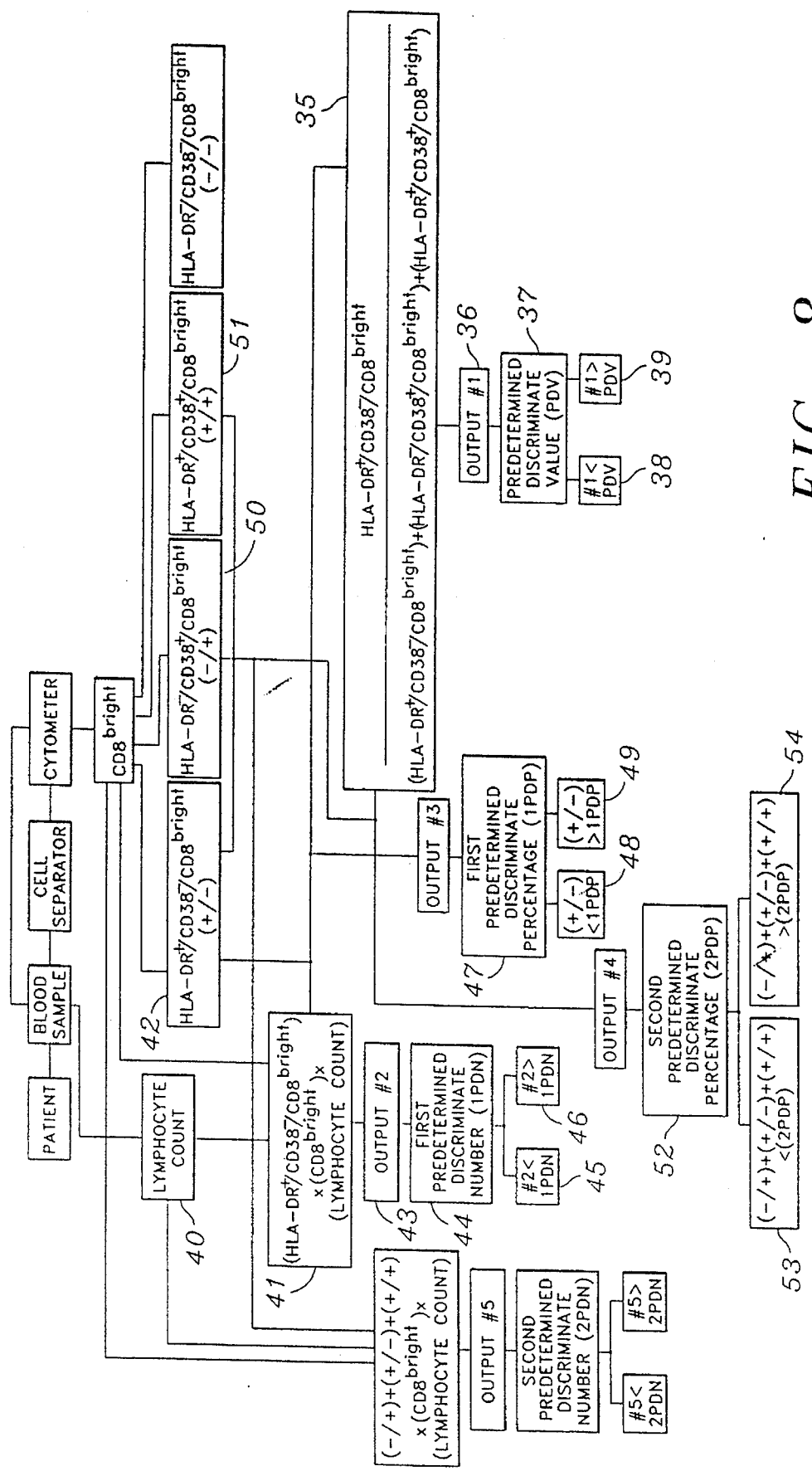
FIG. 8 is a flow diagram illustrating the procedure for determining the requisite representations of data for developing the prognosis of a patient.

FIG. 8 describes the manner of obtaining the requisite information for making a determination of at least one of the indications of having a relatively favorable prognosis, a suppression of HIV, or a stable disease condition.

From a patient, a blood sample may be taken and this is passed through a cell separator and in turn, to a cytometer for obtaining different measurements. The blood sample is also subjected to a lymphocyte count.

First Calculation Method

In a first manner of determining the favorable prognosis, suppression of HIV or stable condition, the following determinations are made. From the flow cytometer, the CD8$^{bright}$ cells are measured. Next, four determinations are made of cells within this category. These are the set HLA-DR$^+$/CD38$^-$/CD8$^{bright}$, HLA-DR$^-$/CD38+/CD8$^{bright}$, HLA-DR$^+$/CD38+/CD8$^{bright}$, and HLA-DR$^{/CD}$38$^-$/CD8$^{bright}$. The latter groups reflected as (−/−) would be the resting group of cells, namely, the cells falling in a Quadrant of a histogram which is the bottom left Quadrant 31 as represented in the histogram 27b of FIG. 7. This is shown as Quadrant 3. The cells falling in the histogram Quadrant 32 (Quadrant 4) of histogram 27b are those designated as (+/−). The cells falling in the histogram Quadrant 33 (Quadrant 2) are those designated as (+/+). The cells falling in the histogram Quadrant 34 (Quadrant 1) are those designed as (−/+). The cells of interest for this calculation are those of the groups (+/−), (−/+), and (+/+), namely (Quadrant 1+Quadrant 2 and Quadrant 4). Of major concern are the cells in group (+/−), namely cells of the set HLA-DR$^+$/CD38$^-$/CD8$^{bright}$ (Quadrant 4). These cells are otherwise designated as HLA-DR$^+$/CD38$^-$/CD8$^{bright}$.

A determination is then made in the box 35 of the ratio $$\frac{\text{HLA-DR}^+/\text{CD38}^-/\text{CD8}^{bright}}{(\text{HLA-DR}^+/\text{CD38}^-/\text{CD8}^{bright}) + (\text{HLA-DR}^-/\text{CD38}^+/\text{CD8}^{bright}) + (\text{HLA-DR}^+/\text{CD38}^+/\text{CD8}^{bright})}$$

The numerator is constituted by the percentage of cells (+/−) and the denominator is by the addition of the percentage of cells (+/−)+(−/+)+(+/+). The latter three groups of percentages of cells are added and constitute the denominator. The output #1 in box 36 is then subjected to a ratio comparison relative to a predetermined discriminate value (PDV) as indicated in box 37. The determination of the prognosis, stable condition or suppression of HIV is made by a determination of whether the results of output #1 are lower than the PDV as indicated in box 38 or higher than the PDV as indicated in box 39. A favorable prognosis, stable condition or suppression of HIV is indicated by results within box 39.

In the manner of this calculation, a relationship is applied between the HLA-DR$^+$/CD38$^-$/CD8$^{bright}$ cells relative to the activated CD8$^{bright}$ cells. This relationship is illustrated in a ratio format.

Second Calculation Method

A second form of effecting the determination would be by an absolute count measure. In this manner, the lymphocyte count 40 is determined from the blood sample and this is related to the CD8$^{bright}$ count as indicated in box 41. Additionally, part of this calculation is a determination of the percentage of cells falling within box 42, namely the HLA-DR$^+$/CD38$^-$/CD8$^{bright}$ cells. The determination is made based on the following calculation:

$$(\text{HLA-DR}^+/\text{CD38}^-/\text{CD8}^{bright}) \times (\text{CD8}^{bright}) \times (\text{Lymphocyte Count})$$

The output from box 41 is designated as output #2 indicated in box 43. The output #2 is compared with a first predetermined discriminate number (1PDN) indicated in box 44 and a determination is made as to whether the output #2 is less than this first predetermined discriminate number as indicated in box 45 or greater than the first predetermined discriminate number as indicated in box 46. In the calculation format being described, the determination is being made based on a measure of cells, namely an absolute number of cells and not a ratio of cells relative to other cells. A relatively favorable prognosis, suppression of HIV or stable condition would be indicated by results falling within block 46, namely an output number #2 greater than the PDV. Block 46 represents a favorable condition. Block 45 represents a poor condition.

Another aspect to the calculation of the absolute number calculation is a determination of an output representing $[(-/+)+(+/-)+(+/+)] \times \text{CD8}^{bright} \times \text{Lymphocyte Count}$ (FIG. 8). This output is given as output #5. This is compared with a second predetermined discriminate number (2PDN). A greater or lesser determination relative to 2PDN would give useful information for favorable progression, stable condition or suppression.

Third Calculation Method

In yet a further form of making the determination, a relationship is described with the reference to either a numerator and denominator characteristic, respectively. In this manner, and as illustrated in FIG. 8, the count cells falling in block 42 are an output number and a first predetermined discriminate percentage (1PDP) as indicated in block 47. This would represent the percentage of cells in Quadrant 4, namely 31 in FIG. 7. A determination is made as to whether the cells from block 42 are less than the 1PDP as indicated in block 48 or greater than the 1PDP as indicated in block 49. The result may give useful information as to the relative favorable prognosis, stable condition or suppression of HIV.

In a different determination, the summation of the cells from block 42, 50, and 51 as output #4 is made. This is a total of the percentage of cells in Quadrants 1, 2 and 4 (namely 34, 33 and 32 in FIG. 7). This total percentage is compared to a second predetermined discriminate percentage (2PDP) in block 52. The comparison is then made as to the summation of the cells in block 42, 50 and 51 as to whether it is less than the 2PDP, as indicated in block 53, or greater than the 2PDP, as indicated in block 54. The outcome of that determination would likely give a determination of a relatively favorable disease condition, stable condition or suppression of HIV. Block 53 indicates a favorable condition. Block 54 indicates a poor condition.

General

Figure 9:
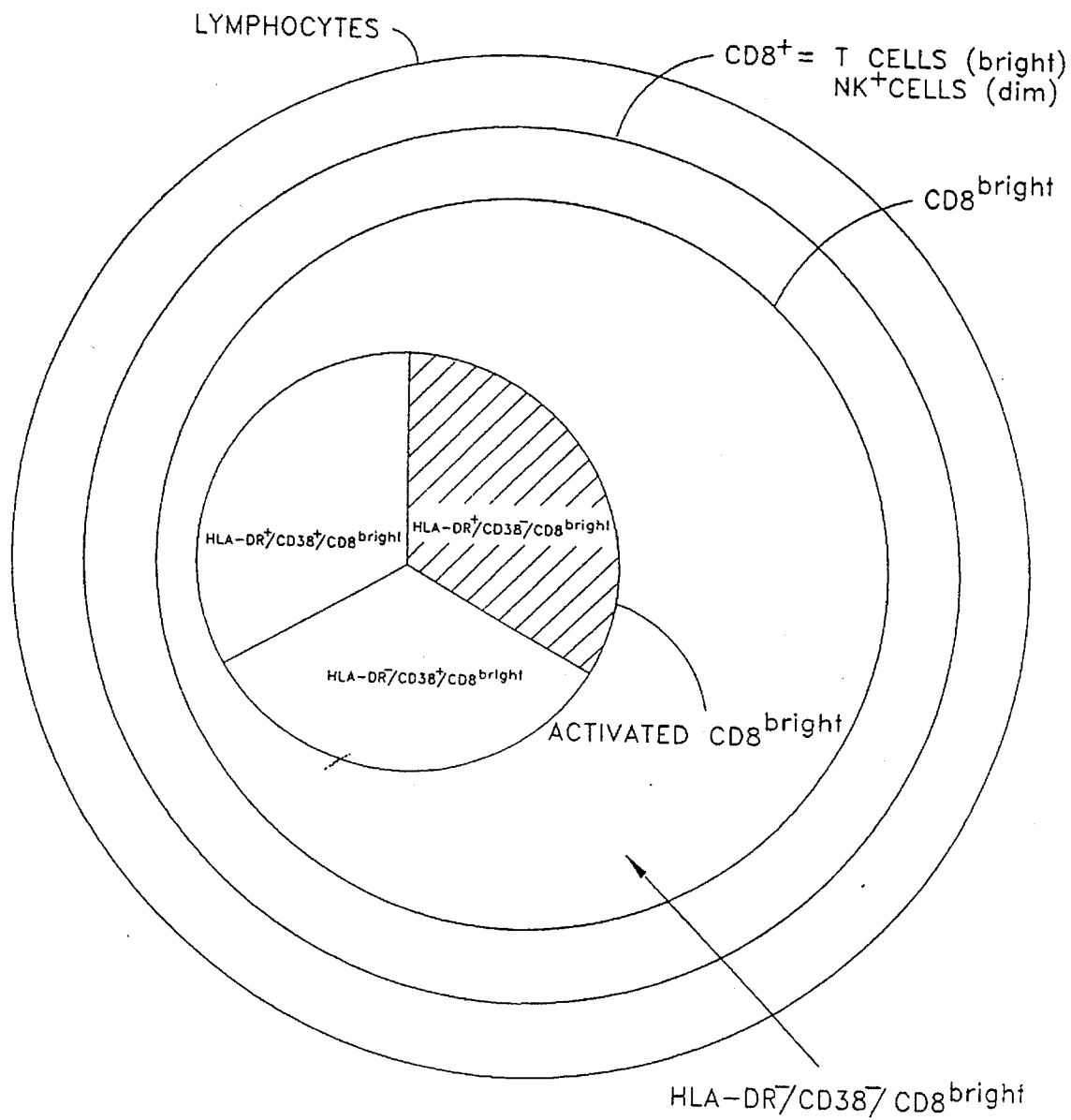
FIG. 9 is a diagrammatic representation of the relationship of different kinds of cells within a lymphocyte population.
Figure 10:
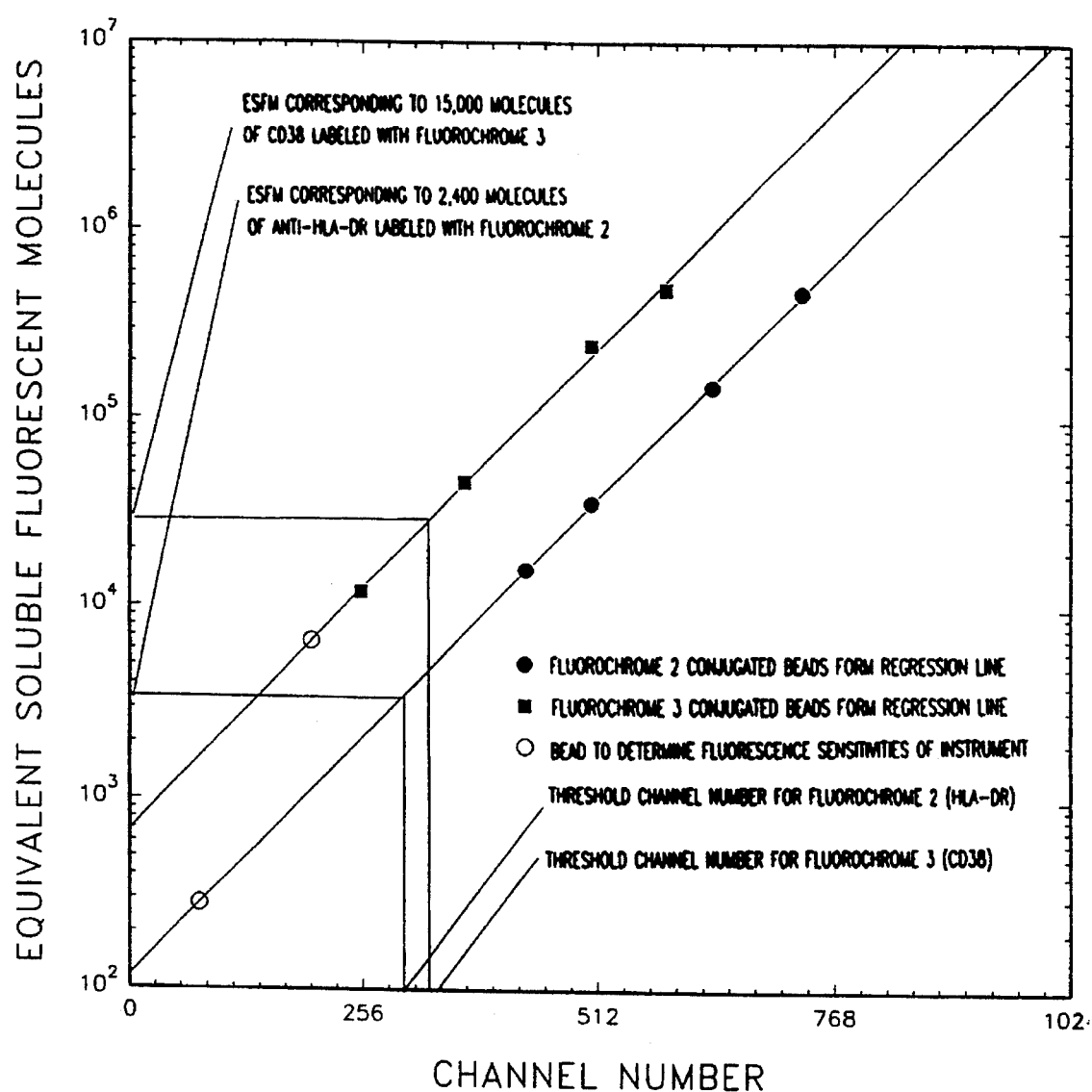
FIG. 10 is a regression line graph showing threshold values for the HLA-DR antigen and CD38 antigen.

An illustration in FIG. 9 describes diagrammatically the relationship of the different cells. Broadly indicated is the lymphocyte group. Within the lymphocytes are a group CD8+, which are the T cells (bright) and NK+ cells (dim). Within that group of cells are the $CD8^{bright}$ and in turn within that group are the activated $CD8^{bright}$ cells. Inside of the activated $CD8^{bright}$ cells, the cells of interest are divided into three groups, namely, the HLA-DR+/CD38−/$CD8^{bright}$, and the associate groups HLA-DR+/CD38+/$CD8^{bright}$, and HLA-DR−/CD38+/$CD8^{bright}$. The resting cells, namely cells outside of the activated $CD8^{bright}$ group, are those indicated as HLA-DR−/CD38−/$CD8^{bright}$ and which fall between the circle indicating activated $CD8^{bright}$ and the circle indicating $CD8^{bright}$.

Many other forms of the invention exist, each differing from the other in matters of detail only.

For instance, the measure of applied relationship of the HLA-DR+/CD38−/$CD8^{bright}$ cells relative to other cell populations can be made in different ways. An indication of a "measure" and "related to" are defined above. In one exemplary alternative manner of representing the data, the first calculation method described in FIG. 8 could be related to a ratio of absolute numbers rather than a ratio of percentages.

The invention has been described with reference to measuring or relating the cells of group HLA-DR+CD38−/$CD8^{bright}$ in relation to the cells in the activated $CD8^{bright}$ group. In other forms, the cells of HLA-DR+/CD38− could be related to cells of larger groups, namely that falling within the $CD^{bright}$ group, or CD8+ group, or lymphocytes. When a comparison is made relative to an increasing number of cells, namely larger and larger circles as diagrammatically illustrated, it is likely that the results would be less informative than as compared to the preferred comparison as indicated. Nonetheless, it will be possible to obtain useful data from these further relationships. As indicated, a determination can be made from a measure or relationship of the HLA-DR+/CD38−/$CD8^{bright}$ cells.

The above description and the examples are illustrative only. The scope of the invention is to be determined solely in terms of the following claims.

TABLE 1

CIRCULATING LEVEL OF CD8 bright CELLS THAT EXPRESS CD38 AND/OR HLA-DR AG[a]

| Subpopulation | CD8 bright Cell Subset | HIV-Neg Controls n = 10 | Asymptomatic HIV-Pos n = 8 | AIDS n = 15 |
| --- | --- | --- | --- | --- |
| 1 | DR−CD38− | 434 ± 155 | 277 ± 130 (0.04) | 175 ± 205 (0.003, NS) |
| 2 | DR+CD38− | 34 ± 25 | 223 ± 115 (0.002) | 93 ± 83 (0.02, 0.005) |
| 3 | DR+CD38+ | 7 ± 3 | 144 ± 132 (0.02) | 253 ± 178 (0.0001, NS) |
| 4 | DR−CD38+ | 54 ± 26 | 71 ± 53 (NS) | 178 ± 56 (0.0001, 0.0002) |

[a]CD4 level (mean ± SD) of HIV-seronegative (HIV-Neg) controls, 962 ± 437/mm³; of asymptomatic HIV-seropositives (HIV-Pos) subjects, 533 ± 283; of AIDS patients, 265 ± 188. Values in the table are CD8+ T cells/mm³ with the indicated phenotype; subpopulations correspond to those illustrated in FIG. 1. Values in parentheses are the p values for a two-sample t-test; p values in the column for asymptomatic HIV-seropositive subjects reflect the test between this group and the HIV-seronegative controls; p values in the column for AIDS patients reflect the test between this group and the HIV-seronegative controls followed by the value for the test between this group and the asymptomatic HIV-seropositive group.

TABLE II

SERUM P24 AND CLINICAL OUTCOMES OF RAPID PROGRESSORS

| Subject | Specimen No.* 1 | 2 | 3 | 4 | 5 | AIDS DX | Interval AIDS | Death |
|---|---|---|---|---|---|---|---|---|
| 1 | −/ND | −/ND | −/− | +/+ | −/− | SC, KS, PCP | 19 | 26 |
| 2 | −/ND | −/ND | −/+ | +/+ | +/+ | NHL | 36 | 38 |
| 3 | −/ND | +/ND | −/− | −/− | −/+ | KS | 41 | 55 |
| 4 | −/ND | −/ND | −/− | −/− | −/+ | CMV | 43 | 67 |
| 5 | −/ND | −/ND | −/+ | −/− | −/− | PCP, CI, CMV | 54 | |
| 6 | −/ND | −/ND | −/− | −/− | −/− | PCP | 61 | |

*Specimens were ordered by time relative to seroconversion. Specimen 3 was the first seropositive sample.
Months from seroconversion to AIDS and from seroconversion to death; subjects 5 and 6 were still alive when this analysis was complete.
SC = systemic candidiasis; KS = Kaposi's Sarcoma; PCP = *Pneumocystis carinii* Pneumonia, CI = Cryptococcal infection, CMV = cytomegalovirus retinitis, NHL = non-Hodgkin's lymphoma.
Free p24/complexed p24; ND, not determined; −, p24 below cutoff; +, p24 above cutoff; the cutoff for free p24 is 7 pg/ml and for complexed p24 is 16 pg/ml.

TABLE III

CD4 AND CD8 NUMBERS/MM$^3$ AND PERCENT OF CD8$^{bright}$ SUBPOPULATIONS AT EACH VISIT IN THE THREE STUDY GROUPS*

| Group/ Specimen No. | ABSOLUTE NUMBER/MM$^3$ CD4 | CD8$^{br}$ | PERCENT OF LYMPHOCYTES DR$^-$CD38$^-$CD8$^{br}$ | DR$^+$CD38$^-$CD8$^{br}$ | DR$^+$CD38$^+$CD8$^{br}$ | DR$^-$CD38$^+$CD8$^{br}$ |
|---|---|---|---|---|---|---|
| Seronegative [n = 16] | | | | | | |
| 1 | 932 ± 322 | 539 ± 200 | 20.0 ± 5.8 | 1.5 ± 1.0 | 1.0 ± 0.7 | 2.9 ± 2.3 |
| 2 | 1003 ± 410 | 578 ± 234 | 20.5 ± 6.4 | 1.5 ± 0.7 | 0.8 ± 0.7 | 2.3 ± 1.5 |
| 3 | 1088 ± 484 | 607 ± 209 | 19.6 ± 5.0 | 1.4 ± .07 | 1.0 ± 0.5 | 3.0 ± 1.7 |
| 4 | 1079 ± 669 | 595 ± 275 | 19.6 ± 4.4 | 1.5 ± 0.6 | 0.9 ± 0.5 | 2.7 ± 1.4 |
| 5 | 965 ± 404 | 554 ± 208 | 19.3 ± 4.8 | 1.3 ± 0.6 | 0.9 ± 0.7 | 2.8 ± 1.4 |
| Seroconverter slow progressor [n = 10] | | | | | | |
| 1 | 1025 ± 436 | 532 ± 135 | 18.5 ± 3.4 | 2.6 ± 2.5 | 1.0 ± 1.0 | 2.1 ± 1.1 |
| 2 | 1130 ± 732 | 828 ± 758 | 19.4 ± 5.1 | 2.7 ± 1.6 | 3.6 ± 7.9 | 2.4 ± 1.8 |
| 3 | 773 ± 232 | 1041 ± 719 | 18.6 ± 6.5 | 3.8 ± 1.8 | 12.3 ± 11.7 | 5.0 ± 3.6 |
| 4 | 667 ± 190 | 924 ± 441 | 19.8 ± 5.1 | 6.1 ± 4.1 | 9.8 ± 6.9 | 5.5 ± 3.7 |
| 5 | 586 ± 204♦ | 944 ± 456 | 20.3 ± 5.7 | 7.0 ± 6.1 | 10.9 ± 8.2 | 6.0 ± 3.4 |
| Seroconverter rapid progressor [n = 6] | | | | | | |
| 1 | 772 ± 411 | 646 ± 281 | 23.8 ± 8.6 | 3.0 ± 1.7 | 2.2 ± 0.8 | 3.6 ± 2.2 |
| 2 | 685 ± 187 | 570 ± 192 | 24.6 ± 7.6 | 3.1 ± 2.2 | 1.9 ± 0.7 | 4.2 ± 3.3 |
| 3 | 612 ± 266 | 1126 ± 566 | 16.3 ± 3.5 | 3.8 ± 1.8 | 17.3 ± 11.3 | 10.6 ± 7.6 |
| 4 | 319 ± 167 | 862 ± 451 | 15.2 ± 5.8 | 3.1 ± 2.0 | 15.7 ± 8.9 | 15.3 ± 8.7 |
| 5 | 250 ± 133♦ | 816 ± 316 | 17.7 ± 7.6 | 2.8 ± 1.8 | 14.5 ± 10.6 | 14.3 ± 7.6 |

*Means ± SD; CD8$^{bright}$ abbreviated CD8$^{br}$.

‡One of the 10 slow progressors had markedly elevated CD8$^{bright}$ cells at visit 2 (absolute CD8$^{bright}$ number 2972/mm$^3$). The elevation was due to a high level (1842/mm$^3$) of HLA-DR$^+$/CD38$^+$ CD8$^{bright}$ cells. The mean CD8$^{bright}$ absolute number for the other nine subjects was 590/mm$^3$ (SD83).
♦The range of CD4 values at visit 5 for the slow progressors was 224–865/mm$^3$ and that for the rapid progressors was 42–444/mm$^3$.

REFERENCES

1. Hoffenbach, A., P. Langlade-Demoyen, G. Dadaglio, E. Vilmer, F. Michel, C. Mayaud, B. Autran, and F. Plata. 1989. Unusually high frequencies of HIV-specific cytotoxic T lymphocytes in humans. J. Immunol. 142:452.

2. Walker, B. D. and F. Plata. 1990. Cytotoxic T lymphocytes against HIV. AIDS 4:177.

3. Nixon, D. F. and A. J. McMichael. 1991. Cytotoxic T-cell recognition of HIV proteins and peptides. AIDS 5:1049.

4. Autran, B. and J. V. Giorgi. 1992. Activated CD8$^{bright}$ cells in HIV-related diseases. In Immunodeficiency in HIV Infection and AIDS. G. Janossy, B. Autran and F. Miedema, eds. Karger, Basel, p. 171.

5. Salazar-Gonzalez, J. F., D. J. Moody, J. V. Giorgi, O. Martinez-Maza, R. T. Mitsuyasu, and J. L. Fahey. 1985. Reduced ecto-5'-nucleotidase activity and enhanced OKT10 and HLA-DR expression on CD8 (T-suppressor/cytotoxic) lymphocytes in the acquired immune deficiency syndrome: Evidence of CD8 cell immaturity. J. Immunol. 135:1778.

6. Giorgi, J. V. and R. Detels. 1989. T-cell subset alterations in HIV-infected homosexual men: NIAID multicenter AIDS cohort study. Clin. Immunol. Immunopathol. 52:10.

7. Yagi, M. J., M. E. Joesten, J. Wallace, J. P. Roboz, and J. G. Bekesi. 1991. Human immunodeficiency virus type 1

(HIV-1) genomic sequences and distinct changes in CD8+ lymphocytes precede detectable levels of HIV-1 antibodies in high-risk homosexuals. J. Infect. Dis. 164:183.

8. Prince, H. E. and E. R. Jensen. 1991. Three-color cytofluorometric analysis of CD8 cell subsets in HIV-1 infection. J. Acquir. Immune Defic. Syndr. 4:1227.

9. Reinherz, E. L., P. O. Kung, G. Goldstein, R. H. Levey, and S. F. Schlossman. 1980. Discrete stages of human intrathymic differentiation: Analysis of normal thymocytes and leukemic lymphoblasts of T-cell lineage. Proc. Natl. Acad. Sci. USA 77:1588.

10. Jackson, D. G. and J. I. Bell. 1990. Isolation of a cDNA encoding the human CD38 (T10) molecule, a cell surface glycoprotein with an unusual discontinuous pattern of expression during lymphocyte differentiation. J. Immunol. 144:2811.

11. Alessio, M., S. Roggero, A. Funaro, L. B. De Monte, L. Peruzzi, M. Geuna, and F. Malavasi. 1990. CD38 molecule: Structural and biochemical analysis on human T lymphocytes, thymocytes, and plasma cells. J. Immunol. 145:878.

12. Gerli, R., P. Rambotti, C. Cernetti, A. Velardi, F. Spinozzi, A. Tabilio, M. F. Martelli, F. Grignani, and S. Davis. 1984. A mature thymocyte-like phenotypic pattern on human cord circulating T-lymphoid cells. J. Clin. Immunol. 4:461.

13. Funaro, A., G. C. Spagnoli, C. M. Ausiello, M. Alessio, S. Roggero, D. Delia, M. Zaccolo, and F. Malavasi. 1990. Involvement of the multilineage CD38 molecule in a unique pathway of cell activation and proliferation. J. Immunol. 145:2390.

14. Kaslow, R. A., D. G. Ostrow, R. Detels, J. P. Phair, B. F. Polk, and C. R. Rinaldo. 1987. The multicenter AIDS cohort study: Rationale, organization, and selected characteristics of the participants. Am. J. Epidemiol. 126:310.

15. Chmiel, J. S., R. Detels, R. A. Kaslow, M. Van Raden, L. A. Kingsley, R. Brookmeyer, and The Multicenter AIDS Cohort Study Group. 1987. Factors associated with prevalent human immunodeficiency virus (HIV) infection in the multicenter AIDS cohort study. Am. J. Epidemiol. 126:568.

16. Lanier, L. L., A. M. Le, J. H. Phillips, N. L. Warner, and G. F. Babcock. 1983. Subpopulations of human natural killer cells defined by expression of the Leu-7 (HNK-1) and Leu-11 (NK-15) antigens. J. Immunol. 131:1789.

17. Schenker, E. L., L. E. Hultin, K. D. Bauer, J. Ferbas, J. B. Margolick, and J. V. Giorgi. 1993. Evaluation of a dual-color flow cytometry immunophenotyping panel in a multicenter quality assurance program. Cytometry, in press.

18. Chakrabarti, S., K. Brechling, and B. Moss. 1985. Vaccinia virus expression vector: Coexpression of b-galactosidase provides visual screening of recombinant virus plaques. Mol. Cell Biol. 5:3403.

19. Flexner, C., S. S. Broyles, P. Earl, S. Chakrabarti, and B. Moss. 1988. Characterization of human immunodeficiency virus gag/pol gene products expressed by recombinant vaccinia viruses. Virology 166:339.

20. Koup, R. A., J. L. Sullivan, P. H. Levine, F. Brewster, A. Mahr, G. Mazzara, S. McKenzie, and D. Panicali. 1989. Antigenic specificity of antibody-dependent cell-mediated cytotoxicity directed against human immunodeficiency virus in antibody-positive sera. J. Virol. 63:584.

21. Pross, H. F., M. G. Baines, P. Rubin, P. Shragge, and M. S. Patterson. 1981. Spontaneous human lymphocyte-mediated cytotoxicity against tumor target cells. IX. The quantitation of natural killer cell activity. J. Clin. Immunol. 1:51.

22. Dixon, W. J. and F. J. Mossey. 1983. Introduction to Statistical Analysis. In Inference: Two Populations. 4th ed. W. J. Dixon and F. J. Mossey, eds. McGraw-Hill Book Co., New York, p. 127.

23. Hollander, M. and D. A. Wolfe. 1973. The one-way layout. In Nonparametric Statistical Methods. M. Hollander and D. A. Wolfe, eds. John Wiley & Sons, New York, p. 114.

24. Neter, J., W. Wasserman, and M. H. Kutner. 1985. Random and mixed effects models for two factor studies. In Applied Linear Statistical Models. Irwin, Homewood, p. 784.

25. Miller, R. G., Jr. 1981. Simultaneous Statistical Inference. Springer Verlag, New York.

26. Plata, F., B. Autran, L. P. Martins, S. Wain-Hobson, M. Raphael, C. Mayaud, M. Denis, J-M. Guillon, and P. Debra. 1987. AIDS virus-specific cytotoxic T lymphocytes in lung disorders. Nature 328:348.

27. Joly, P., J. -M. Guillon, C. Mayaud, F. Plata, I. Theodorou, M. Denis, P. Debré, and B. Autran. 1989. Cell-mediated suppression of HIV-specific cytotoxic T lymphocytes. J. Immunol. 143:2193.

28. Walker, B. D., S. Chakrabarti, B. Moss, T. J. Paradis, T. Flynn, A. G. Durno, R. S. Blumberg, J. C. Kaplan, M. S. Hirsch, and R. T. Schooley. 1987. HIV-specific cytotoxic T lymphocytes in seropositive individuals. Nature 328:345.

29. Koup, R. A., J. L. Sullivan, P. H. Levine, D. Brettler, A. Mahr, G. Mazzara, S. McKenzie, and D. Panicali. 1989. Detection of major histocompatibility complex class I-restricted HIV-specific cytotoxic T lymphocytes in the blood of infected hemophiliacs. Blood 73:1909.

30. Walker, B. D., C. Flexner, T. J. Paradis, T. C. Fuller, M. S. Hirsch, R. T. Schooley, and B. Moss. 1988. HIV-1 reverse transcriptase is a target for cytotoxic T lymphocytes in infected individuals. Science 240:64.

31. Nixon, D. F., A. R. M. Townsend, J. G. Elvin, C. R. Rizza, J. Gallwey, and A. J. McMichael. 1988. HIV-1 gag-specific cytotoxic T lymphocytes defined with recombinant vaccinia virus and synthetic peptides. Nature 336:484.

32. Gotch, F. M., D. F. Nixon, N. Alp, A. J. McMichael, and L. K. Borysiewicz. 1990. High frequency of memory and effector gag specific cytotoxic T lymphocytes in HIV seropositive individuals. Int. Immunol. 2:707.

33. Culmann, B., E. Gomard, M-. P. Kieny, B. Guy, F. Dreyfus, A. G. Saimot, D. Sereni, D. Sicard, and J-. P. Levy. 1991. Six epitopes reacting with human cytotoxic CD8+ T cells in the central region of the HIV-1 nef protein. J. Immunol. 146:1560.

34. Riviere, Y., F. Tanneau-Salvadori, A. Regnault, O. Lopez, P. Sansonetti, B. Guy, M. -P. Kieny, J. -J. Fournel, and L. Montagnier. 1989. Human immunodeficiency virus-specific cytotoxic responses of seropositive individuals: Distinct types of effector cells mediate killing of targets expressing gag and env proteins. J. Virol. 63:2270.

35. Koenig, S., P. Earl, D. Powell, G. Pantaleo, S. Merli, B. Moss, and A. S. Fauci. 1988. Group-specific, major histocompatibility complex class I-restricted cytotoxic responses to human immunodeficiency virus 1 (HIV-1) envelope proteins by cloned peripheral blood T cells from an HIV-1-infected individual. Proc. Natl. Acad. Sci. USA 85:8638.

36. Koenig, S., T. R. Fuerst, L. V. Wood, R. M. Woods, J. A. Suzich, G. M. Jones, V. F. de la Cruz, R. T. Davey, Jr., S.

Venkatesan, B. Moss, W. E. Biddison, and A. S. Fauci. 1990. Mapping the fine specificity of a cytolytic T cell response to HIV-1 nef protein. J. Immunol. 145:127.

37. Takahashi, K., L-. C. Dai, T. R. Fuerst, W. E. Biddison, P. L. Earl, B. Moss, and F. A. Ennis. 1991. Specific lysis of human immunodeficiency virus type 1-infected cells by a HLA-A3.1-restricted CD8+ cytotoxic T-lymphocyte clone that recognizes a conserved peptide sequence within the gp41 subunit of the envelope protein. Proc. Natl. Acad. Sci. USA 88:10277.

38. Sethi, K. K., H. Näher, and I. Stroehmann. 1988. Phenotypic heterogeneity to cerebrospinal fluid-derived HIV-specific and HLA-restricted cytotoxic T-cell clones. Nature 335:178.

39. Weinhold, K. J., H. K. Lyerly, T. J. Matthews, D. S. Tyler, P. M. Ahearne, K. C. Stine, A. J. Langlois, D. T. Durack, and D. P. Bolognesi. 1988. Cellular anti-gp120 cytolytic reactivities in HIV-1 seropositive individuals. Lancet i:902.

40. McChesney, M., F. Tanneau, A. Regnault, P. Sansonetti, L. Montagnier, M. P. Kieny, and Y. Riviere. 1990. Detection of primary cytotoxic T lymphocytes specific for the envelope glycoprotein of HIV-1 by deletion of the env amino-terminal signal sequence. Eur. J. Immunol. 20:215.

41. Orentas, R. J., J. E. K. Hildreth, E. Obah, M. Polydefkis, G. E. Smith, M. L. Clements, and R. F. Siliciano. 1990. Induction of CD4+ human cytolytic T cells specific for HIV-infected cells by a gp160 subunit vaccine. Science 248:1234.

42. Tyler, D. S., S. D. Stanley, C. A. Nastala, A. A. Austin, J. A. Bartlett, K. C. Stine, H. K. Lyerly, D. P. Bolognesi, and K. J. Weinhold. 1990. Alterations in antibody-dependent cellular cytotoxicity during the course of HIV-1 infection: Humoral and cellular defects. J. Immunol. 144:3375.

43. Miedema, F., M. Tersmette, and R. A. W. Van Lier. 1990. AIDS pathogenesis: a dynamic interaction between HIV and the immune system. Immunol. Today 11:293.

44. Leclerc, J. -C. and H. Cantor. 1980. T cell-mediated immunity to oncornavirus-induced tumors. II. Ability of different T cell sets to prevent tumor growth in vivo. J. Immunol. 124:851.

45. Prince, H. E. and C. D. Czaplicki. 1989. Preferential loss of Leu 8-, CD45R-, HLA-DR+ CD8 cell subsets during in in vitro culture of mononuclear cells from human immunodeficiency virus type I (HIV)-seropositive former blood donors. J. Clin. Immunol. 9:421.

46. Tsubota, H., C. I. Lord, D. I. Watkins, C. Morimoto, and N. L. Letvin. 1989. A cytotoxic T lymphocyte inhibits acquired immunodeficiency syndrome virus replication in peripheral blood lymphocytes. J. Exp. Med. 169:1421.

47. Aranda-Anzaldo, A. 1991. A role for CD8+ T lymphocytes in the pathogenesis of AIDS. Res. Immunol. 142:541.

48. Koup, R. A., C. A. Pikora, K. Luzuriaga, D. B. Brettler, E. S. Day, G. P. Mazzara, and J. L. Sullivan. 1991. Limiting dilution analysis of cytotoxic T lymphocytes to human immunodeficiency virus gag antigens in infected persons: In vitro quantitation of effector cell populations with p17 and p24 specificities. J. Exp. Med. 174:1593.

49. Walker, C. M., D. J. Moody, D. P. Stites, and J. A. Levy. 1986. CD8+ lymphocytes can control HIV infection in vitro by suppressing virus replication. Science 234:1563.

50. Brinchmann, J. E., G. Gaudernack, and F. Vartdal. 1990. CD8+ T cells inhibit HIV replication in naturally infected CD4+ T cells: Evidence for a soluble inhibitor. J. Immunol. 144:2961.

51. Hausner, M. A., J. V. Giorgi, and S. Plaeger-Marshall. 1992. A reproducible method to detect CD8 T cell mediated inhibition of HIV production from naturally infected CD4 cells. J. Immunol. Methods, 157:181.

52. Hercend, T., J. Ritz, S. F. Schlossman, and E. L. Reinherz. 1981. Comparative expression of T9, T10, and Ia antigens on activated human T cell subsets. Hum. Immunol. 3:247.

53. Pantaleo, G., A. De Maria, S. Koenig, L. Butini, B. Moss, M. Baseler, H. C. Lane, and A. S. Fauci. 1990. CD8+ T lymphocytes of patients with AIDS maintain normal broad cytolytic function despite the loss of human immunodeficiency virus-specific cytotoxicity. Proc. Natl. Acad. Sci. USA 87:4818.

54. Tomkinson, B. E., R. Maziarz, and J. L. Sullivan. 1989. Characterization of the T cell-mediated cellular cytotoxicity during acute infectious mononucleosis. J. Immunol. 143:660.

55. Pantaleo, G., S. Koenig, M. Baseler, H. C. Lane, and A. S. Fauci. 1990. Defective clonogenic potential of CD8+ T lymphocytes in patients with AIDS: Expansion in vivo of a nonclonogenic CD3+CD8+DR+CD25- T cell population. J. Immunol. 144:1696.

56. Prince, H. E., S. Kleinman, C. Czaplicki, J. John, and A. E. Williams. 1990. Interrelationships between serologic markers of immune activation and T lymphocyte subsets in HIV infection. J. Acquir. Immune Defic. Syndr. 3:525.

57. Giorgi, J. V., J. L. Fahey, D. C. Smith, L. E. Hultin, H. -L. Cheng, R. T. Mitsuyasu, and R. Detels. 1987. Early effects of HIV on CD4 lymphocytes in vivo. J. Immunol. 138:3725–3730.

58. Lang, W., H. Perkins, R. E. Anderson, R. Royce, N. Jewell, and W. Winkelstein, Jr. 1989. Patterns of T lymphocyte changes with human immunodeficiency virus infection: From seroconversion to the development of AIDS. J. Acquir. Immune Defic. Syndr. 2:63–69.

59. Fahey, J. L., J. M. G. Taylor, R. Detels, B. Hofmann, R. Melmed, P. Nishanian, and J. V. Giorgi. 1990. The prognostic value of cellular and serologic markers in infection with human immunodeficiency virus type 1. N. Engl. J. Med. 322:166–172.

60. Moss, A. R., P. Bacchetti, D. Osmond, W. Krampf, R. E. Chaisson, D. Stites, J. Wilber, J-P. Allain, and J. Carlson. 1988., Seropositivity for HIV and the development of AIDS or AIDS related condition: Three-year follow up of the San Francisco General Hospital cohort. Br. Med. J. 296:745–750.

61. Cooper, D. A., B. Tindall, E. J. Wilson, A. A. Imrie, and R. Penny. 1988., Characterization of T lymphocyte responses during primary infection with human immunodeficiency virus. J. Infect. Dis. 157:889–896.

62. Ziegler-Heitbrock, H. W. L., D. Stachel, T. Schlunk, L. Gürtler, W. Schramm, M. Fröschl, J. R. Bogner, and G. Riethmüller. 1988. Class II (DR) antigen expression on CD8+ lymphocyte subsets in acquired immune deficiency syndrome (AIDS). J. Clin. Immunol. 8:1–6.

63. Bogner, J. R., A. Matuschke, B. Heinrich, M. A. Schreiber, C. Nerl, and F-D. Goebel. 1990. Expansion of activated T lymphocytes (CD3+HLA/DR+) detectable in early stages of HIV-1 infection. Klin. Wochenschr. 68:393–396.

64. Mackewicz, C. E., H. W. Ortega, and J. A. Levy. 1991. CD8+ cell anti-HIV activity correlates with the clinical state of the infected individual. J. Clin. Invest. 87:1462–1466.

65. Taylor, J., R. Afrasiabi, J. L. Fahey, E. Korns, M. Weaver, and R. Mitsuyasu. 1986. Prognostically significant classification of immune changes in AIDS with Kaposi's Sarcoma. Blood 67:666–671.

66. Polk. B. F., R. Fox, R. Brookmeyer, S. Kancharanaraksa, R. Kaslow, B. Visscher, C. R. Rinaldo, and J. P. Phair. 1987. Predictors of the acquired immunodeficiency syndrome developing in a cohort of seropositive homosexual men. N. Engl. J. Med. 316:61–66.

67. Nishanian, P., K. R. Huskins, S. Stehn, R. Detels, and J. L. Fahey. 1990. A simple method for improved assay demonstrates that HIV p24 antigen is present as immune complexes in most sera from HIV-infected individuals. J. Infect. Dis. 162:21–28.

68. Whitton, J. L. and M. B. A. Oldstone. 1990. Virus-induced immune response interactions; Principles of immunity and immunopathology. In Virology. 2nd ed. B. N. Fields and D. M. Knipe, editors. Raven Press, New York. 369–381.

69. Quinnan, G. V., Jr., N. Kirmani, A. H. Rook, J. F. Manischewitz, L. Jackson, G. Moreschi, G. W. Santos, R. Saral, and W. H. Burns. 1982., Cytotoxic T cells in cytomegalovirus infection. N. Engl. J. Med. 307:7–13.

70. McMichael, A. J., F. M. Gotch, G. R. Noble, and P. A. S. Beare. 1983. Cytotoxic T-cell immunity to influenza. N. Engl. J. Med. 309:13–17.

71. Oldstone, M. B. A., P. Blount, P. J. Southern, and P. W. Lampert. 1986. Cytoimmunotherapy for persistent virus infection reveals a unique clearance pattern from the central nervous system. Nature 321:239–243.

72. Reddehase, M. J., S. Jonjic, F. Weiland, W. Mutter, and U. H. Koszinowski. 1988. Adoptive immunotherapy of murine cytomegalovirus andrenalitis in the immunocomprised host: CD4-helper-independent antiviral function of CD8-positive memory T lymphocytes derived from latently infected donors. J. Virol. 62:1061–1065.

73. Fahey, J. L., H. Prince, M. Weaver, J. Groopman, B. Visscher, K., Schwartz, and R. Detels. 1984. Quantitative changes in T helper or T suppressor/cytotoxic lymphocyte subsets that distinguish acquired immune deficiency syndrome from other immune subset disorders. Am. J. Med. 76:95–100.

74. Walker, C. M. and J. A. Levy. 1989. A diffusible lymphokine produced by CD8$^+$ T lymphocytes suppresses HIV replication. J. Immunol. 66:628–630.

75. Evans, R. L., T. J. Faldetta, R. E. Humphreys, D. M. Pratt, E. J. Yunis, and S. F. Schlossman. 1978. Peripheral human T cells sensitized in mixed leukocyte culture synthesize and express Ia-like antigens. J. Exp. Med. 148:1440–1445.

76. Allain, J. -P., D. A. Paul, Y. Laurian, D. Senn, and Members of the AIDS-Haemophilia French Study Group. 1986. Serological markers in early stages of human immunodeficiency virus infection in haemophiliacs. Lancet ii:1233–1236.

77. Goudsmit, J., F. De Wolf, D. A. Paul, L. G. Epstein, J. M. A. Lange, W. J. A. Krone, H. Speelman, E. C. Wolters, J. Van Der Noordaa, J. M. Oleske, H. J. Van Der Helm, and R. A. Coutinho. 1986. Expression of human immunodeficiency virus antigen (HIV-Ag) in serum and cerebrospinal fluid during acute and chronic infection. Lancet ii:177–180.

78. Coombs, R. W., A. C. Collier, J-P. Allain, B. Nikora, M. Leuther, G. F. Gjerset, and L. Corey. 1989. Plasma viremia in human immunodeficiency virus infection. N. Engl. J. Med. 321:1626–1631.

79. Stramer, S. L., J. S. Heller, R. W. Coombs, J. V. Parry, D. D. Ho, and J.-P. Allain. 1989. Markers of HIV infection prior to IgG antibody seropositivity. J. Am Med. Assoc. 262:64–69.

80. The. T. H. and Feltkamp, T. E. W. 1970a. Conjugation of Fluorescein Isothiocyanate to Antibodies. I. Experiments on the Conditions of Conjugation. Immunology 18:865–873.

81. The, T. H. and Feltkamp, T. E. W. 1970b. Conjugation of Fluorescein Isothiocyanate to Antibodies. II. A Reproducible Method. Immunology 18:875–881.

What is claimed is:

1. A method for determining a favorable prognosis in an HIV positive subject which comprises quantitatively detecting an elevated level of HLA-DR$^+$/CD38$^-$/CD8$^{bright}$ cells thereby determining a favorable prognosis in the HIV positive subject.

2. A method as claimed in claim 1, wherein in the elevated level of HLA-DR$^+$/CD38$^-$/CD8$^{bright}$ cells, the cells have relatively greater levels of HLA-DR antigen and relatively less CD38 antigen relative to a threshold for each of the HLA-DR and CD38 antigens, and applying a relationship between the elevated HLA-DR$^+$/CD38$^-$/CD8$^{bright}$ cell levels relative to the activated CD8$^{bright}$ cells, the relationship being a diagnostic evaluation of the relatively favorable prognosis in the HIV positive subject.

3. A method as claimed in claim 1, wherein the elevated level of HLA-DR$^+$/CD38$^-$/CD8$^{bright}$ cells is determined relative to a number of activated CD8$^{bright}$ cells present.

4. A method as claimed in claim 3, wherein a determination of HLA-DR$^+$/CD38$^-$/CD8$^{bright}$ cells constitutes a numerator in a relationship with the number of activated CD8$^{bright}$ cells, such number of activated CD8$^{bright}$ cells constituting a denominator in the relationship.

5. A method as claimed in claim 3, wherein a score of HLA-DR$^+$ /CD38$^-$/CD8$^{bright}$ cells is determined and is represented as a first cell count, and wherein a score of activated CD8$^{bright}$ cells is determined and is represented as a second cell count such that when the number of cells in the first cell count relative to the number of cells in the second cell count is greater than a first discriminate value, this is determinative of a favorable prognosis.

6. A method as claimed in claim 3 including relating a percentage of the HLA-DR$^+$/CD38$^-$/CD8$^{bright}$ cells relative to activated CD8$^{bright}$ cells and applying a relationship of this percentage as a diagnostic evaluation of the condition.

7. A method as claimed in claim 3 wherein a favorable prognosis of the condition is determined in relation to an increased level of HLA-DR$^+$/CD38$^-$/CD8$^{bright}$ cells relative to the level of activated CD8$^{bright}$ cells.

8. A method of diagnosing a stable disease condition associated with HIV in a human comprising:
   (a) obtaining a blood sample from the human;
   (b) testing the sample by determining at least one measure of an activated CD8$^{bright}$ cell population having HLA-DR$^+$/CD38$^-$ /CD8$^{bright}$ cells;
   (c) applying a relationship between the HLA-DR$^+$/CD38$^-$/CD8$^{bright}$ cell population in relation to an activated CD8$^{bright}$ cell population as a diagnostic evaluation of a favorable prognosis of the disease condition; and
   (d) presenting such relationship thereby diagnosing a stable disease condition associated with HIV in the human.

9. A method as claimed in claim 8 including determining a cell population with relatively greater HLA-DR antigen and relatively less CD38 antigen relative to a threshold for each of the HLA-DR and CD38 antigens, and applying this determination relative to the activated $CD8^{bright}$ cells as a diagnostic evaluation of the stable disease condition associated with HIV infection in the human.

10. A method as claimed in claim 9, wherein a score of $HLA\text{-}DR^+/CD38^-/CD8^{bright}$ cells is determined and is represented as a first cell count, and wherein a score of activated $CD8^{bright}$ cells is determined and is represented as a second cell count such that when the number of cells in the first cell count is greater than a first predetermined discriminate number and the number of cells in the second cell count is lower than a second predetermined discriminate number, this is determinative of a favorable prognosis.

11. A method as claimed in claim 9 wherein a score of $HLA\text{-}DR^+/CD38^-/CD8^{bright}$ cells is determined and is represented as a first cell count, such that when the number of cells in the first cell count is greater than a first predetermined discriminate number (1PDN), this is determinative of a favorable prognosis.

12. A method as claimed in claim 9 wherein a score of $HLA\text{-}DR^+/CD38^-/CD8^{bright}$ cells is determined and is represented as a first cell count, such that when the number of cells in the first cell count is greater than a second predetermined discriminate number (2PDN), this is determinative of a favorable prognosis.

13. A method as claimed in claim 8 including relating a percentage of the $HLA\text{-}DR^+/CD38^-/CD8^{bright}$ cells relative to the percentage of activated $CD8^{bright}$ cells, and applying a relationship of this percentage as a diagnostic evaluation of the stable disease condition associated with HIV in the human.

14. A method as claimed in claim 8, wherein a determination of $HLA\text{-}DR^+/CD38^-/CD8^{bright}$ cells constitutes a numerator in a relationship with the number of activated $CD8^{bright}$ cells, such number of activated $CD8^{bright}$ cells constituting a denominator in the relationship.

15. A method as claimed in claim 8 including relating a percentage of the $HLA\text{-}DR^+/CD38^-/CD8^{bright}$ cells relative to activated $CD8^{bright}$ cells and applying a relationship of this percentage as a diagnostic evaluation of the stable disease condition associated with HIV disease in the human.

16. A method as claimed in claim 8 wherein a favorable prognosis of the condition is determined in relation to an increased level of $HLA\text{-}DR^+/CD38^-/CD8^{bright}$ cells relative to the level of activated $CD8^{bright}$ cells.

17. A method for monitoring the course of disease in an HIV positive subject which comprises quantitatively determining in a first cell sample from the subject the presence of $HLA\text{-}DR^+/CD38^-/CD8^{bright}$ cells and comparing the amount so determined with the amount present in a second sample from the subject, such samples being taken at different points in time, a difference in the amounts determined being indicative of the course of disease.

18. A method as claimed in claim 17, wherein the presence of $HLA\text{-}DR^+/CD38^-/CD8^{bright}$ cells is determined in relation to a number of activated $CD8^{bright}$ cells present.

19. A method of diagnosing a disease condition related to HIV in a human comprising:

(a) obtaining a blood sample from the human, (b) determining from the sample at least one measure of an activated $CD8^{bright}$ cell population having $HLA\text{-}DR^+/CD38^-/CD8^{bright}$ cells, (c) presenting such measure, and (d) applying the measure of the $HLA\text{-}DR^+/CD38^-/CD8^{bright}$ cell population selectively as at least one of a diagnostic evaluation of a favorable prognosis of a disease condition, a stable disease condition or condition of inhibition of HIV replication.

20. A method as claimed in claim 19 including determining a cell population with relatively greater HLA-DR antigen and relatively less CD38 antigen relative to a threshold for each of the HLA-DR and CD38 antigens, and applying a measure of the $HLA\text{-}DR^+/CD38^-/CD8^{bright}$ cell population above the threshold relative to an activated $CD8^{bright}$ cell population 21. A method as claimed in claim 20 including relating a percentage of the $HLA\text{-}DR^+/CD38^-/CD8^{bright}$ cell population of relatively greater concentration relative to a percentage of activated $CD8^{bright}$ cells, and applying a relationship of this percentage as an evaluation of the condition.

22. A method as claimed in claim 19 including relating a percentage of the $HLA\text{-}DR^+/CD38^-/CD8^{bright}$ cell population of relatively greater concentration relative to a percentage of activated $CD8^{bright}$ cells, and applying a relationship of this percentage as an evaluation of the condition.

23. A method as claimed in claim 14, wherein a favorable prognosis of the condition is determined in relation to an increased level of $HLA\text{-}DR^+/CD38^-/CD8^{bright}$ cells relative to activated $CD8^{bright}$ cells.

24. A method as claimed in claim 19, wherein a determination of $HLA\text{-}DR^+/CD38^-/CD8^{bright}$ cells constitutes a numerator in a relationship with the number of activated $CD8^{bright}$ cells, such number of activated $CD8^{bright}$ cells constituting a denominator in the relationship.

25. A method of diagnosing a disease condition related to HIV in a human comprising:

(a) obtaining a blood sample from the human, (b) determining from the sample at least one measure of an activated $CD8^{bright}$ cell population having $HLA\text{-}DR^+/CD38^-/CD8^{bright}$ cells in the sample, (c) applying a relationship between the $HLA\text{-}DR^+/CD38^+/CD8^{bright}$ cell population in relation to a $CD8^+$ lymphocyte population as a diagnostic evaluation of at least one of a favorable prognosis of the disease condition, a stable condition or suppressor of HIV replication; and (d) presenting such relationship.

26. A method as claimed in claim 25 including determining a cell population with relatively greater HLA-DR antigen and relatively less CD38 antigen relative to a threshold for each of the HLA-DR and CD38 antigens, and applying a measure of $HLA\text{-}DR^+/CD38^-/CD8^{bright}$ cells in a relationship with this threshold and relative to the activated $CD8^{bright}$ cells as an evaluation of the disease condition.

27. A method of diagnosing a disease condition related to HIV infection in a human comprising:

(a) obtaining a blood sample from the human, (b) determining from the sample at least one measure of a lymphocyte population having a $HLA\text{-}DR^+/CD38^-/CD8^{bright}$ cell, (c) applying a relationship between the $HLA\text{-}DR^+/CD38^-/CD8^{bright}$ cell population and the lymphocyte population as at least one of a diagnostic evaluation of the prognosis of a favorable disease condition, a stable condition or an HIV suppression condition, and (d) presenting such relationship.

28. The method as claimed in claim 25 or 27, wherein the measure is a ratio, percentage, absolute number, product, difference or quotient.

29. The method as claimed in claim 21, wherein the lymphocyte population is selected from a group consisting of a $CD8^+$ cell, a $CD8^{bright}$ cell, or an activated $CD8^{bright}$ cell.

* * * * *

UNITED STATES PATENT AND TRADEMARK OFFICE
CERTIFICATE OF CORRECTION

PATENT NO. : 5,470,701  
DATED : November 28, 1995  
INVENTOR(S) : Giorgi et al.

Page 1 of 5

It is certified that error appears in the above-identified patent and that said Letters Patent is hereby corrected as shown below:

Column 1, line 29, insert --deficiency-- after the word "immune"

Column 2, line 41, "CD38/CD8bright cells" should read --$CD38^-$/$CD^{bright}$ cells--

Column 4, lines 9, 22 & 25, delete "T" after the word "bright"

Column 4, line 30, "(DR+CD38+)" should read --($DR^+CD38^+$)--

Column 4, line 38, "±" should read --+--

Column 4, line 40, "(_____)" should read --(---)--

Column 4, line 41, "$CD38^{-1}$/$^{CD}8^{bright}$" should read --$CD38^-$/$CD8^{bright}$--

Column 4, line 41, "$DR^-$" should read --$DR^+$--

Column 4, line 42, "$DR^{-/CD}38^+$" should read --$DR^-$/$CD38^+$--

Column 5, line 18, " " CD8 cells" mean cells that express" should read -- "CD8 positive cells" or "$CD8^+$ cells" mean cells that express--

UNITED STATES PATENT AND TRADEMARK OFFICE
CERTIFICATE OF CORRECTION

PATENT NO. : 5,470,701

DATED : November 28, 1995

INVENTOR(S) : Giorgi et al.

It is certified that error appears in the above-identified patent and that said Letters Patent is hereby corrected as shown below:

Column 5, line 43, delete "." after the word "must"

Column 6, line 10, insert --(2PDP)-- after the word "percentage".

Column 6, line 11, delete "(2PDP)" after the word "percentage".

Column 7, line 39, "This" does not start a new paragraph

Column 7, line 44, "CD38⁻" should read --CD38--

Column 7, lines 45 & 46 "antigens, and applying this" should read --antigens. This--

Column 13, lines 61 & 62, insert --a score of-- after the word "representing"

Column 13, line 65, insert --(1PDN)-- after the word "number"

Column 14, line 39, insert --CD8-- after the word "the"

Column 14, line 40, insert --Additionally, the first population is HLA-DR$^+$ and the second population is CD38$^-$ and the CD8$^+$ lymphocyte is CD8$^{bright}$.-- after the word "bright"

UNITED STATES PATENT AND TRADEMARK OFFICE
CERTIFICATE OF CORRECTION

PATENT NO. : 5,470,701

DATED : November 28, 1995

INVENTOR(S) : Giorgi et al.

It is certified that error appears in the above-identified patent and that said Letters Patent is hereby corrected as shown below:

Column 14, line 57, insert --T-- after the word "$CD8^+$"

Column 19, lines 59 & 65, delete "T" after the word "$CD8^{bright}$"

Column 20, lines 41, 47, 52 & 61, delete "T" after the word "bright"

Column 20, line 64, delete "T" after the word "bright"

Column 20, lines 27 & 28, "(7±3) activated" should read --(7+3)--

Column 20, line 55, "$CD8^+$" should read --$CD8^{bright}$--

Column 21, line 12, delete "$CD8^+$" after the word "$CD38^+$"

Column 21, lines 66 and 67, "$^d CD8^{bright}$" should read --/$CD8^{bright}$--.

Column 22, line 56, "Antigert" should read --Antigen--

Column 23, line 36, delete "T" after the word "bright"

UNITED STATES PATENT AND TRADEMARK OFFICE
CERTIFICATE OF CORRECTION

PATENT NO. : 5,470,701

DATED : November 28, 1995

INVENTOR(S) : Giorgi et al.

It is certified that error appears in the above-identified patent and that said Letters Patent is hereby corrected as shown below:

Column 23, line 51, "Table III" should start a new paragraph

Column 24, lines 67 & 24, "DR+" should read --$DR^+$--

Column 25, line 51, "delete "T" after the word "bright"

Column 27, lines 27 & 28, "CD38+" should read --$CD38^+$--

Column 27, line 28, "$DR^{/CD}38^-$" should read --$DR^-/CD38^-$--

Column 29, line 24, "DR+" should read --$DR^+$--

Column 31, line 5, insert --◆-- after the letters "DX"

Column 31, line 4, insert --↕-- after the word "Interval"

Column 31, line 6, insert --⊗-- after the letters "ND" (first occurrence)

UNITED STATES PATENT AND TRADEMARK OFFICE
CERTIFICATE OF CORRECTION

PATENT NO. : 5,470,701
DATED : November 28, 1995
INVENTOR(S) : Giorgi et al.

It is certified that error appears in the above-identified patent and that said Letters Patent is hereby corrected as shown below:

Column 31, line 14, insert --↕-- before the word "Months"

Column 31, line 16, insert --◆-- before the letters "SC"

Column 31, line 18, insert --⊗-- before the word "Free"

Column 31, line 15, insert --↕-- after the numerals "758"

Column 33, line 7, "P.O." should read --P.C.--

Column 34, line 17, "Debra" should read --Debré--

Signed and Sealed this

Twenty-sixth Day of May, 1998

Attest:

BRUCE LEHMAN

*Attesting Officer*     *Commissioner of Patents and Trademarks*